US007734483B1

(12) United States Patent
Smith et al.

(10) Patent No.: US 7,734,483 B1
(45) Date of Patent: Jun. 8, 2010

(54) COMPUTER IMPLEMENTED METHOD AND SYSTEM FOR ANALYZING PHARMACEUTICAL BENEFIT PLANS AND FOR PROVIDING MEMBER SPECIFIC ADVICE, OPTIONALLY INCLUDING LOWER COST PHARMACEUTICAL ALTERNATIVES

(75) Inventors: Jack A. Smith, Franklin Lakes, NJ (US); Thomas E. Feitel, Franklin Lakes, NJ (US); Brian W. Cavanagh, Franklin Lakes, NJ (US); Vicente L. Caride, New York, NY (US); Giovanni C. Minardi, Franklin Lakes, NJ (US); Shannon Sue Scullin, Franklin Lakes, NJ (US); John E. Gobinski, Franklin Lakes, NJ (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 371 days.

(21) Appl. No.: 11/804,890

(22) Filed: May 21, 2007

Related U.S. Application Data

(60) Provisional application No. 60/802,196, filed on May 20, 2006.

(51) Int. Cl.
*A61B 5/00* (2006.01)
*G06F 19/00* (2006.01)
(52) U.S. Cl. .......................................................... 705/3
(58) Field of Classification Search .................. 705/2, 705/3
See application file for complete search history.

(56) References Cited

U.S. PATENT DOCUMENTS

| 5,737,539 | A | * | 4/1998 | Edelson et al. ............... 705/3 |
| 5,758,095 | A | * | 5/1998 | Albaum et al. ............... 705/2 |
| 6,000,828 | A | * | 12/1999 | Leet .............................. 705/2 |
| 7,124,031 | B1 | | 10/2006 | Hoffman et al. |
| 2001/0034613 | A1 | | 10/2001 | Rubsamen |
| 2001/0037216 | A1 | | 11/2001 | Oscar et al. |
| 2002/0052760 | A1 | * | 5/2002 | Munoz et al. ............... 705/2 |
| 2002/0095314 | A1 | | 7/2002 | Bodsworth et al. |
| 2002/0111832 | A1 | * | 8/2002 | Judge ........................... 705/3 |

(Continued)

OTHER PUBLICATIONS

Keys, PW et al., "Computer-guided academic detailling as part of a drug benefit program," AM J Health Syst Pharm, vol. 15; pp. 2199-2203; discussion 22034 (Oct. 15, 1995).

(Continued)

*Primary Examiner*—Gerald J. O'Connor
*Assistant Examiner*—Trang Nguyen
(74) *Attorney, Agent, or Firm*—Irah H. Donner; Wilmer Cutler Pickering Hale and Dorr LLP

(57) ABSTRACT

A method is described for reducing medication purchasing costs for a member of a pharmaceutical benefits plan. A member's currently prescribed medications are analyzed, and at least one substitute medication is recommended for the analyzed medication, this recommendation is based the member's pharmaceutical benefit plan. In response to the recommendation, the system receives at least one of an authorization and selection of a substitute medication. Approval for this medication is requested from the member's doctor. Further, the requested approval is sent along with a plurality of other medication substitution requests. The responses are processed to complete the substitution of the medication for the member. The member is informed that the substitute medication was approved for their purchase.

35 Claims, 32 Drawing Sheets

U.S. PATENT DOCUMENTS

| | | |
|---|---|---|
| 2003/0009367 A1 * | 1/2003 | Morrison ........................ 705/9 |
| 2006/0095300 A1 | 5/2006 | Schrier et al. |
| 2006/0136272 A1 | 6/2006 | Rubsamen |
| 2006/0265245 A1 | 11/2006 | McCallie et al. |
| 2007/0067186 A1 | 3/2007 | Brenner et al. |
| 2008/0021735 A1 | 1/2008 | Elizabeth et al. |
| 2008/0021736 A1 | 1/2008 | Elizabeth et al. |

OTHER PUBLICATIONS

Noffsitner R et al., "Improving the delivery of Care and reducing Healthcare Costs with digitization of Information," Journal of Healthcare Information Management, vol. 14; pp. 23-30 (Summer 2000).

* cited by examiner

HOW IT MIGHT WORK ONLINE

RX PLAN ENROLLMENT

PART 1: PERSONAL AND PHYSICIAN INFORMATION

MEMBER INFORMATION — 702 — CHANGE

CHRIS BELL
DATE OF BIRTH: 11/11/1976

123 MAIN STREET
ANYTOWN, ST 12345

ALSO COVERED BY YOUR PRESCRIPTION BENEFIT — 704

| NAME, GENDER, DATE OF BIRTH | CHANGE |
| NAME, GENDER, DATE OF BIRTH | CHANGE |
| NAME, GENDER, DATE OF BIRTH | CHANGE |

PHYSICIAN INFORMATION — 706

LAURA STEVENS, M.D.
144 ELM ST.
ANYTOWN, ST 12345                    CHANGE

CHARLES BARRINGER, M.D.
300 WINDING PATH LN.
ANYTOWN, ST 12340                    CHANGE

JAMES CARMICHAEL, M.D.
108 SCHOOLHOUSE RD
ANYTOWN, ST 12340                    CHANGE

ELLEN TREAT, M.D.
1243 HIGH ST.
ANYTOWN, ST 12388                    CHANGE

CONTINUE TO PART 2 >>

FIG. 7

RX PLAN ENROLLMENT

PART 2: PREFERENCES FOR CONTINUED SAVINGS AND HIGH QUALITY OF CARE

CONTINUE TO SAVE MONEY WHILE MAINTAINING THE HIGHEST QUALITY OF CARE BY INDICATING YOUR DISPENSING PREFERENCES WHEN NEW PRESCRIPTIONS ARE REQUESTED IN THE FUTURE.

ALL REQUESTS TO CHANGE A PRESCRIPTION MUST BE APPROVED BY YOU AND YOUR PHYSICIAN BEFORE THEY BECOME EFFECTIVE.

DISPENSING PREFERENCES

WITH MY PHYSICIAN'S APPROVAL:              LEARN MORE ABOUT THIS OPTION

- 802 — ALWAYS DISPENSE A LOWER COST GENERIC MEDICATION WHEN AVAILABLE    ⦿YES  ◯NO
- 804 — ALWAYS PROVIDE 90 DAYS OF THERAPY THROUGH MEDCO BY MAIL FOR LONG-TERM MEDICATIONS   ⦿YES  ◯NO
- 806 — ALWAYS NOTIFY ME IF I AM PRESCRIBED A MORE EXPENSIVE, NON-PREFERRED, OR NOT COVERED MEDICATION   ⦿YES  ◯NO

CONTINUE TO PART 3 >>

FIG. 8

| MY RX CHOICES HOMEPAGE - MEDICARE |
|---|

TERMS OF USE | PRIVACY | VIEW MESSAGES | LOGOUT

MEDCO® | PRESCRIPTIONS & BENEFITS | HEALTH & WELLNESS | NONPRESCRIPTION ITEMS

GO TO: PRESCRIPTIONS                                  ITEMS IN CART: 1 VIEW DETAILS

MY RX CHOICES                         HAVE A QUESTION? NEED HELP? LEARN MORE >>
START SAVING MONEY ON YOUR PRESCRIPTIONS NOW.
USE MY RX CHOICES, THE PRESCRIPTIONS SAVINGS PROGRAM THAT LETS YOU HELP
YOUR DOCTOR SAVE YOU MONEY ON MEDICATIONS YOU TAKE ON AN ONGOING BASIS.*

— 902

SELECT THE MEDICATIONS YOU ARE STILL TAKING:
THE DRUGS LISTED BELOW ARE MEDICATIONS YOU CURRENTLY TAKE ON AN ONGOING BASIS.
CHECK THE BOX NEXT TO THE MEDICATIONS FOR WHICH YOU'D LIKE TO REVIEW LOWER-COST ALTERNATIVES,
THEN CLICK THE "CONTINUE" BUTTON.

CONSUMER REPORTS
BEST BUY DRUGS

NEW! PROVEN,
EFFECTIVE, AFFORDABLE
OPTIONS FROM
CONSUMER REPORTS
BEST BUY DRUGS

LEARN MORE NOW

| CURRENT PRESCRIPTIONS FOR CHRIS | STRENGTH |
|---|---|
| ☑ PROTONIX — 904 | 40 MG TABLET |
| ☑ ALLEGRA | 60 MG TABLET — 910 |
| ☑ LIPITOR | 40 MG TABLET |
| ☐ ACCUPRIL | 5 MG TABLET |

( CONTINUE ) — 906

908 ~• CAN'T FIND A DRUG?
    SEARCH FOR OTHER DRUGS NOT LISTED ABOVE.
    VIEW RECENTLY SEARCHED DRUGS >>

*NO CHANGES TO YOUR MEDICATIONS SHOULD BE MADE WITHOUT PHYSICIAN APPROVAL. SOME OR ALL OF THE ALTERNATIVES PRESENTED MAY NOT BE APPROPRIATE, AND THERE MAY BE OTHERS THAN THOSE LISTED.

SOME ALTERNATIVES MAY NOT REPRESENT THE RECOMMENDATIONS OF MEDCO'S INDEPENDENT PHARMACY AND THERAPEUTICS COMMITTEE.

PRICES DISPLAYED FOR BOTH BRAND AND GENERIC MEDICATIONS ARE BASED ON PLAN DESIGN. THE QUANTITY AND DAYS SUPPLY WERE USED TO CALCULATE AN ESTIMATED PRICE. MEDICATION PRICES MAY CHANGE AND YOUR ACTUAL QUANTITY AND/OR DAYS SUPPLY MAY VARY. STATE AND FEDERAL DISPENSING GUIDELINES OR HOW THE MEDICATION IS PACKAGED MAY IMPACT THE QUANTITY AND/OR DAYS SUPPLY YOU CAN RECEIVE. SALES TAX, WHEN APPLICABLE, IS NOT INCLUDED IN THIS PRICING.

PRICES DISPLAYED FOR OVER-THE-COUNTER ALTERNATIVES REFLECT THE ESTIMATED RETAIL PRICE. PLEASE CHECK WITH YOU LOCAL ESTABLISHMENT TO VERIFY THE PRICES FOR THESE PRODUCTS. SALES TAX, WHEN APPLICABLE, IS NOT INCLUDED IN THIS PRICE.

YOUR SAVINGS, IS CALCULATED USING THE PRICE YOU WOULD PAY FOR THE PRESCRIPTION ON A GIVEN DAY, WHETHER IN RETAIL OR MAIL. POTENTIAL SAVINGS MAY VARY BASED ON DEDUCTIBLES, BENEFIT CAPS, PLAN DESIGN, OR THE DIFFERENT COVERAGE STAGES YOU MAY BE IN, ALL OF WHICH MAY CHANGE THROUGHOUT THE YEAR. PLEASE REFER TO YOUR EVIDENCE OF COVERAGE AND SUMMARY OF BENEFITS FOR MORE INFORMATION ON PLAN COSTS AND DETAILS.

THE PRICES DO NOT REFLECT ANY COSTS FOR CLAIMS THAT ARE STILL BEING PROCESSED OR ADJUSTED, OR FOR CLAIMS THAT ARE NOT COVERED MEDICARE PART D PRESCRIPTIONS. THE PRICES AND SAVINGS DISPLAYED MAY CHANGE DAILY.

CHOOSING A LOWER COST ALTERNATIVE MAY RESULT IN MEDCO RECEIVING REBATES. THESE MAY BE SHARED IN SOME MANNER WITH YOUR PLAN DEPENDING ON ITS CONTRACT.

MEDCO MAY CONTACT YOU TO OFFER ASSISTANCE IN CONNECTION WITH MY RX CHOICES.

FIG. 9

| MY RX CHOICES RESULTS PAGE | | | | |
|---|---|---|---|---|
| MEDCO® PRESCRIPTIONS & BENEFITS HEALTH & WELLNESS NONPRESCRIPTION ITEMS TERMS OF USE | PRIVACY | VIEW MESSAGES | LOGOUT | | | | |
| GO TO: PRESCRIPTIONS • MY RX CHOICES | | | ITEMS IN CART: 1 VIEW DETAILS | |
| MY RX CHOICES | | | HAVE A QUESTION? NEED HELP? LEARN MORE >> | |
| CHOOSE ALTERNATIVES FOR YOUR DOCTOR TO CONSIDER AND CLICK THE "CONTINUE" BUTTON TO GO TO THE NEXT STEP. FOR YOUR CONVENIENCE, WE'VE PRESELECTED THE LOWEST-COST MEDICATION ALTERNATIVES AVAILABLE AT THIS TIME. THERE MAY BE MULTIPLE LOWER-COST ALTERNATIVES. <br> • TO REVIEW OTHER ALTERNATIVES, WHICH COULD HAVE THE SAME OR SIMILAR PRICING, CLICK THE "VIEW OTHER ALTERNATIVES" LINK FOR EACH MEDICATION. <br> • TO REMAIN ON YOUR CURRENT MEDICATION, SELECT THE RADIO BUTTON TO THE LEFT OF THE MEDICATION NAME. | | | | |
| IF YOU RECEIVED A LETTER FROM MEDCO REGARDING POTENTIAL SAVINGS USING MY RX CHOICES, THE SAVINGS MAY BE DIFFERENT FROM WHAT IS DISPLAYED BELOW.* | | | | |
| MEDICATION | YOU PAY | LOWER-COST CHOICE 1210 | YOU PAY | YOU SAVE |
| ○ PROTONIX 40 MG TABLET (BRAND) DOSAGE: 1 TABLET, ONCE A DAY PHARMACY: RETAIL 1202 • COVERAGE RULES MAY APPLY • HOW MUCH DOES MY PLAN PAY? • GET DIFFERENT RESULTS WITH DIFFERENT DAYS' SUPPLY AND QUANTITY | $480.00 1206 PER YEAR $40.00 FOR 30 DAYS 1226 | ◉ OMEPRAZOLE 20 MG TABLET 1208 (GENERIC ALTERNATIVE) DOSAGE: 1 TABLET, ONCE A DAY PHARMACY: MEDCO BY MAIL 1212 • COVERAGE RULES MAY APPLY • HOW MUCH DOES MY PLAN PAY? • COMPARE DRUG INFORMATION | $40.00 PER YEAR 1214 $10.00 FOR 90 DAYS 1216 | $440.00 PER YEAR ▷ EXPLAIN MY SAVINGS VIEW OTHER ALTERNATIVES |
| ○ ALLEGRA 60 MG TABLET (BRAND) DOSAGE: 1 TABLET, ONCE A DAY PHARMACY: RETAIL 1224 • COVERAGE RULES MAY APPLY • HOW MUCH DOES MY PLAN PAY? • GET DIFFERENT RESULTS WITH DIFFERENT DAYS' SUPPLY AND QUANTITY | $434.16 PER YEAR $36.18 FOR 30 DAYS | ◉ FEXOFENADINE 60 MG TABLET (GENERIC EQUIVALENT) DOSAGE: 1 TABLET, ONCE A DAY PHARMACY: MEDCO BY MAIL • COVERAGE RULES MAY APPLY • HOW MUCH DOES MY PLAN PAY? • COMPARE DRUG INFORMATION | $40.00 PER YEAR $10.00 FOR 90 DAYS | $394.16 PER YEAR ▷ EXPLAIN MY SAVINGS VIEW OTHER ALTERNATIVES |
| ○ LIPITOR 40 MG TABLET (BRAND) DOSAGE: 1 TABLET, ONCE A DAY BEST BUY DRUGS VIEW REPORT>> PHARMACY: RETAIL • COVERAGE RULES MAY APPLY • HOW MUCH DOES MY PLAN PAY? • GET DIFFERENT RESULTS WITH DIFFERENT DAYS' SUPPLY AND QUANTITY | $300.00 PER YEAR $25.00 FOR 30 DAYS | ◉ SIMVASTATIN 80 MG TABLET (GENERIC ALTERNATIVE) DOSAGE: 1 TABLET, ONCE A DAY BEST BUY DRUGS VIEW REPORT>> PHARMACY: MEDCO BY MAIL • COVERAGE RULES MAY APPLY • HOW MUCH DOES MY PLAN PAY? • COMPARE DRUG INFORMATION | $40.00 PER YEAR $10.00 FOR 90 DAYS | $260.00 PER YEAR ▷ EXPLAIN MY SAVINGS VIEW OTHER ALTERNATIVES 1218 |
| | | | SAVINGS PER YEAR: | $1,094.16 |
| << PREVIOUS    I WANT MY DOCTOR TO REVIEW THE CHOICES LISTED ABOVE FOR A SAVINGS OF <<TOTAL    CONTINUE 1222             ANNUAL SAVINGS OF THE USER SELECTIONS>> OUT OF A POSSIBLE <<TOTAL ANNUAL                       SAVINGS OF LOWEST-COST ALTERNATIVES>> PER YEAR BASED ON TODAYS' PRICES.    1220 | | | | |
| *POTENTIAL SAVINGS ARE CALCULATED USING TODAY'S PRICING. PRICES MAY CHANGE THROUGHOUT THE YEAR. ANY POTENTIAL SAVINGS MAY ALSO VARY BASED ON DEDUCTIBLES, BENEFIT CAPS, PLAN DESIGN, OR ANY OTHER PLAN LIMITATIONS, ALL OF WHICH MAY CHANGE THROUGHOUT THE YEAR. SOME ALTERNATIVES MAY NOT REPRESENT THE RECOMMENDATIONS OF MEDCO'S INDEPENDENT PHARMACY AND THERAPEUTICS COMMITTEE. ALSO, CHOOSING LOWER COST ALTERNATIVES MAY RESULT IN MEDCO RECEIVING REBATES. U.S. PATENT PENDING | | | | |

FIG. 12

RX PLAN ENROLLMENT

PART 2: PHARMACIST RECOMMENDATION AND OTHER ALTERNATIVES
YOU CAN KEEP THE PHARMACIST'S RECOMMENDATION OR CHOOSE A MORE EXPENSIVE ALTERNATIVE FROM THE LIST BELOW.

YOU WILL SAVE: $480.00/YR
YOUR PLAN WILL SAVE: $97.24/YR

PHARMACIST RECOMMENDATION

| | YOU PAY | | PLAN PAYS | |
|---|---|---|---|---|
| | RETAIL (30 DAYS' SUPPLY) | MEDCO BY MAIL (90 DAYS' SUPPLY) | | |
| RANITIDINE HCl 300MG (1320) | ○ $8.26 $99.12/YR (1314) | ● $0.00 $0.00/YR (1312, 1322) | RETAIL: $0.00<br>MAIL: $63.26 | EXPLAIN MY COST<br>VIEW DRUG INFORMATION |

1302

OVER-THE-COUNTER ALTERNATIVE

| | YOU PAY | | PLAN PAYS | |
|---|---|---|---|---|
| | RETAIL (65 DAYS' SUPPLY) | MEDCO BY MAIL (65 DAYS' SUPPLY) | | |
| ZANTAC 150MG (65 TABLET PACKAGE) (1314) | ○ $21.99* $131.94/YR | ○ $19.73* $118.38/YR | RETAIL: $0.00<br>MAIL: $0.00 | EXPLAIN MY COST<br>VIEW DRUG INFORMATION |

1304

OTHER RECOMMENDED PRESCRIPTIONS

| | YOU PAY | | PLAN PAYS | |
|---|---|---|---|---|
| | RETAIL (30 DAYS' SUPPLY) | MEDCO BY MAIL (90 DAYS' SUPPLY) | | |
| ZANTAC 300MG (CURRENT PRESCRIPTION) (1316) | ○ $40.00 $480.00/YR | ○ $50.00 $200.00/YR | RETAIL: $29.19<br>MAIL: $134.98 | EXPLAIN MY COST<br>VIEW DRUG INFORMATION |
| AXID 150MG (1308) | ○ $40.00 $480.00/YR | ○ $50.00 $200.00/YR | RETAIL: $40.02<br>MAIL: $164.78 | EXPLAIN MY COST<br>VIEW DRUG INFORMATION |
| PEPCID 40MG (1310) | ○ $40.00 $480.00/YR | ○ $50.00 $200.00/YR | RETAIL: $61.95<br>MAIL: $225.15 | EXPLAIN MY COST<br>VIEW DRUG INFORMATION |

1306

( SUBMIT )

FIG. 13

| MY RX CHOICES WHO WILL CONTACT DOCTOR PAGE | | | | |
|---|---|---|---|---|
| colspan=5 | TERMS OF USE \| PRIVACY \| VIEW MESSAGES \| LOGOUT |

MEDCO® | PRESCRIPTIONS & BENEFITS | HEALTH & WELLNESS | NONPRESCRIPTION ITEMS

GO TO: PRESCRIPTIONS • MY RX CHOICES     ITEMS IN CART: 1 VIEW DETAILS

MY RX CHOICES     HAVE A QUESTION? NEED HELP? LEARN MORE >>

WITH YOUR DOCTOR'S APPROVAL, YOU CAN START SAVING MONEY ON YOUR MEDICATIONS.
REVIEW THE INFORMATION BELOW FOR ACCURACY AND CLICK THE "CONTINUE" BUTTON TO GO TO THE NEXT STEP.
    SCROLL TO CONTINUE ↓

MEDCO CAN CONTACT YOUR DOCTOR FOR THE FOLLOWING CHOICES BECAUSE:
▷ BOTH THE CHOICE LISTED BELOW AND YOUR CURRENT MEDICATION ARE GENERIC EQUIVALENTS
▷ AND, YOU CHOSE UP TO A 90-DAY SUPPLY THROUGH MEDCO BY MAIL   —1406   1412
    LEARN MORE ABOUT WHY MEDCO CAN CONTACT YOUR DOCTOR FOR THESE SAVINGS CHOICES

| CURRENT PRESCRIPTION | YOUR CHOICE | WHO WILL CONTACT MY DOCTOR? | MY DOCTOR IS: |
|---|---|---|---|
| ALLEGRA 60 MG TABLET (BRAND) DOSAGE: 1 TABLET, ONCE A DAY — 1402 | FEXOFENADINE 60 MG TABLET (GENERIC EQUIVALENT) DOSAGE: 1 TABLET, ONCE A DAY — 1404 YOU SAVE: $394.16 PER YEAR | ● MEDCO WILL CONTACT YOUR DOCTOR. LEARN MORE ○ YOU WILL CONTACT YOUR DOCTOR — 1410 | DR. SUSAN JOHNSTON 455 ANYSTREET FRANKLIN LAKES, NJ 07417 (201) 269-3400 — 1408 ▷ UPDATE DOCTOR INFORMATION |

YOU MUST CONTACT YOUR DOCTOR FOR THE FOLLOWING CHOICES BECAUSE:
▷ EITHER THE CHOICE LISTED BELOW A GENERIC ALTERNATIVE TO YOUR MEDICATION
▷ OR, YOU CHOSE TO RECEIVE YOUR MEDICATION FROM A PARTICIPATING RETAIL PHARMACY
▷ OR, YOU CHOSE TO REVIEW A MEDICATION THAT YOU ARE NOT CURRENTLY TAKING
▷ OR, YOU CHOSE TO REVIEW A MEDICATION THAT IS CONSIDERED A CONTROLLED SUBSTANCE    1418
    LEARN MORE ABOUT WHY MUST CONTACT YOUR DOCTOR FOR THESE SAVINGS CHOICES

| CURRENT PRESCRIPTION | YOUR CHOICE | WHO WILL CONTACT MY DOCTOR? |
|---|---|---|
| PROTONIX 40 MG TABLET (BRAND) DOSAGE: 1 TABLET, ONCE A DAY — 1414 | OMEPRAZOLE 20 MG TABLET (GENERIC ALTERNATIVE) DOSAGE: 1 TABLET, ONCE A DAY YOU SAVE: $440.00 PER YEAR | ● YOU WILL CONTACT YOUR DOCTOR LEARN MORE THE INFORMATION YOU NEED WILL BE GIVEN TO YOU AT THE END OF THIS PROCESS. — 1424 |
| ZANAX 10 MG TABLET (BRAND) (CONTROLLED SUBSTANCE) DOSAGE: 1 TABLET, ONCE A DAY — 1416 | ALAZOPRAM 20 MG TABLET (GENERIC ALTERNATIVE) (CONTROLLED SUBSTANCE) DOSAGE: 1 TABLET, ONCE A DAY YOU SAVE: $250.00 PER YEAR | ● YOU WILL CONTACT YOUR DOCTOR LEARN MORE THE INFORMATION YOU NEED WILL BE GIVEN TO YOU AT THE END OF THIS PROCESS — 1426 |

1420                                                                       1422

(<< PREVIOUS)       THE INFORMATION ABOVE IS CORRECT       (CONTINUE)

*POTENTIAL SAVINGS ARE CALCULATED USING TODAY'S PRICING. PRICES MAY CHANGE THROUGHOUT THE YEAR. ANY POTENTIAL SAVINGS MAY ALSO VARY BASED ON DEDUCTIBLES, BENEFIT CAPS, PLAN DESIGN, OR ANY OTHER PLAN LIMITATIONS, ALL OF WHICH MAY CHANGE THROUGHOUT THE YEAR.

SOME ALTERNATIVES MAY NOT REPRESENT THE RECOMMENDATIONS OF MEDCO'S INDEPENDENT PHARMACY AND THERAPEUTICS COMMITTEE. ALSO, CHOOSING LOWER COST ALTERNATIVES MAY RESULT IN MEDCO RECEIVING REBATES.
U.S. PATENT PENDING

FIG. 14

MY RX CHOICES REVIEW CHOICES PAGE

TERMS OF USE | PRIVACY | VIEW MESSAGES | LOGOUT

MEDCO® | PRESCRIPTIONS & BENEFITS | HEALTH & WELLNESS | NONPRESCRIPTION ITEMS

GO TO: PRESCRIPTIONS • MY RX CHOICES

MY RX CHOICES                        HAVE A QUESTION? NEED HELP? LEARN MORE >>

SHOPPING CART
FEXOFENADINE TABS 60
VIEW CART DETAILS
(CHECKOUT)

FOLLOW THESE STEPS TO COMPLETE YOUR REQUEST:
BASED ON YOUR BENEFIT PLAN AND TODAY'S PRICES, YOUR CHOICES, ONCE APPROVED BY YOUR DOCTOR, COULD SAVE YOU $XX.XX

SCROLL TO CONTINUE ↓

FIRST, PRINT YOUR SAVINGS KIT TO BRING TO YOUR DOCTOR.*   (VIEW/PRINT KIT)
PLEASE NOTE: YOU MUST PRINT THIS KIT NOW BEFORE LEAVING THIS PAGE.                    ~1504
WHAT IS IN THE SAVINGS KIT AND WHAT DO YOU DO WITH IT?
  • OMEPRAZOLE 20 MG TABLET (GENERIC ALTERNATIVE)
  • SIMVASTATIN 80 MG TABLET (GENERIC ALTERNATIVE)
                                                                                        ~1510
                    TALKING TO YOUR DOCTOR COULD SAVE YOU: $700.00

1502                                         SCROLL TO CONTINUE ↓

THEN, COMPLETE YOUR REQUEST            (COMPLETE REQUEST)  ~1508

MEDCO WILL CONTACT YOUR DOCTOR FOR APPROVAL FOR THE CHOICES BELOW.
WE WILL NOT CHARGE YOUR CREDIT CARD UNTIL YOUR PRESCRIPTION HAS BEEN FILLED AND SHIPPED FROM ONE OF MEDCO'S MAIL ORDER PHARMACIES.

• FEXOFENADINE 60 MG TABLET (GENERIC EQUIVALENT)                                      ~1512
              ALLOWING MEDCO TO CONTACT YOUR DOCTOR COULD SAVE YOU: $394.16

~1506

AFTER YOU PRINT THE SAVINGS KIT, YOU CAN REVIEW AND CHOOSE LOWER-COST SAVINGS FOR OTHER HOUSEHOLD MEMBERS.

*POTENTIAL SAVINGS ARE CALCULATED USING TODAY'S PRICING. PRICES MAY CHANGE THROUGHOUT THE YEAR. ANY POTENTIAL SAVINGS MAY ALSO VARY BASED ON DEDUCTIBLES, BENEFIT CAPS, PLAN DESIGN, OR ANY OTHER PLAN LIMITATIONS, ALL OF WHICH MAY CHANGE THROUGHOUT THE YEAR.

SOME ALTERNATIVES MAY NOT REPRESENT THE RECOMMENDATIONS OF MEDCO'S INDEPENDENT PHARMACY AND THERAPEUTICS COMMITTEE. ALSO, CHOOSING LOWER COST ALTERNATIVES MAY RESULT IN MEDCO RECEIVEING REBATES.

* TO PRINT THIS INFORMATION, YOU WILL NEED THE ADOBE® READER® PLUG-IN. IF YOU DO NOT HAVE THIS PLUG-IN, YOU WILL NEED TO DOWNLOAD A FREE COPY FIRST.

[GET ADOBE READER]

FIG. 15

CAN GREEN DAY HELP INCREASE PHYSICIAN RESPONSE?           10/14/2005

PATIENT REQUESTS
PHYSICIAN: DR. J. STEVENS
PLAN: MEDICAL MUTUAL
VIEW FORMULARY

| PATIENT | M/F | DOB | CURRENT RX INFO | REQUEST | ACTION |
|---|---|---|---|---|---|
| ANDERSON, FRANK | M | 02/27/1938 | ZANTAC 300 MG RETAIL PHARMACY | RANITIDINE 300 MG MAIL ORDER PHARMACY VIEW REQUEST DETAILS | APPROVED ▽ |
| BARUSO, MAUDE | F | 11/16/1936 | DRUG NAME DELIVERY CHANNEL | SAME DRUG NAME NEW DELIVERY CHANNEL VIEW REQUEST DETAILS | MUST SEE PATIENT ▽ |
|  |  |  | DRUG NAME DELIVERY CHANNEL | NEW DRUG NAME SAME DELIVERY CHANNEL VIEW REQUEST DETAILS | SELECT AN ACTION... ▽ SELECT AN ACTION... APPROVED DENIED MUST SEE PATIENT |
| BELL, CHRIS | M | 08/22/1970 | DRUG NAME DELIVERY CHANNEL | NEW DRUG NAME NEW DELIVERY CHANNEL VIEW REQUEST DETAILS | SELECT AN ACTION... ▽ |
| REIZLER, SANDRA | F | 09/12/1946 | DRUG NAME DELIVERY CHANNEL | NEW DRUG NAME SAME DELIVERY CHANNEL VIEW REQUEST DETAILS | SELECT AN ACTION... ▽ |

SUBMIT

FIG. 16

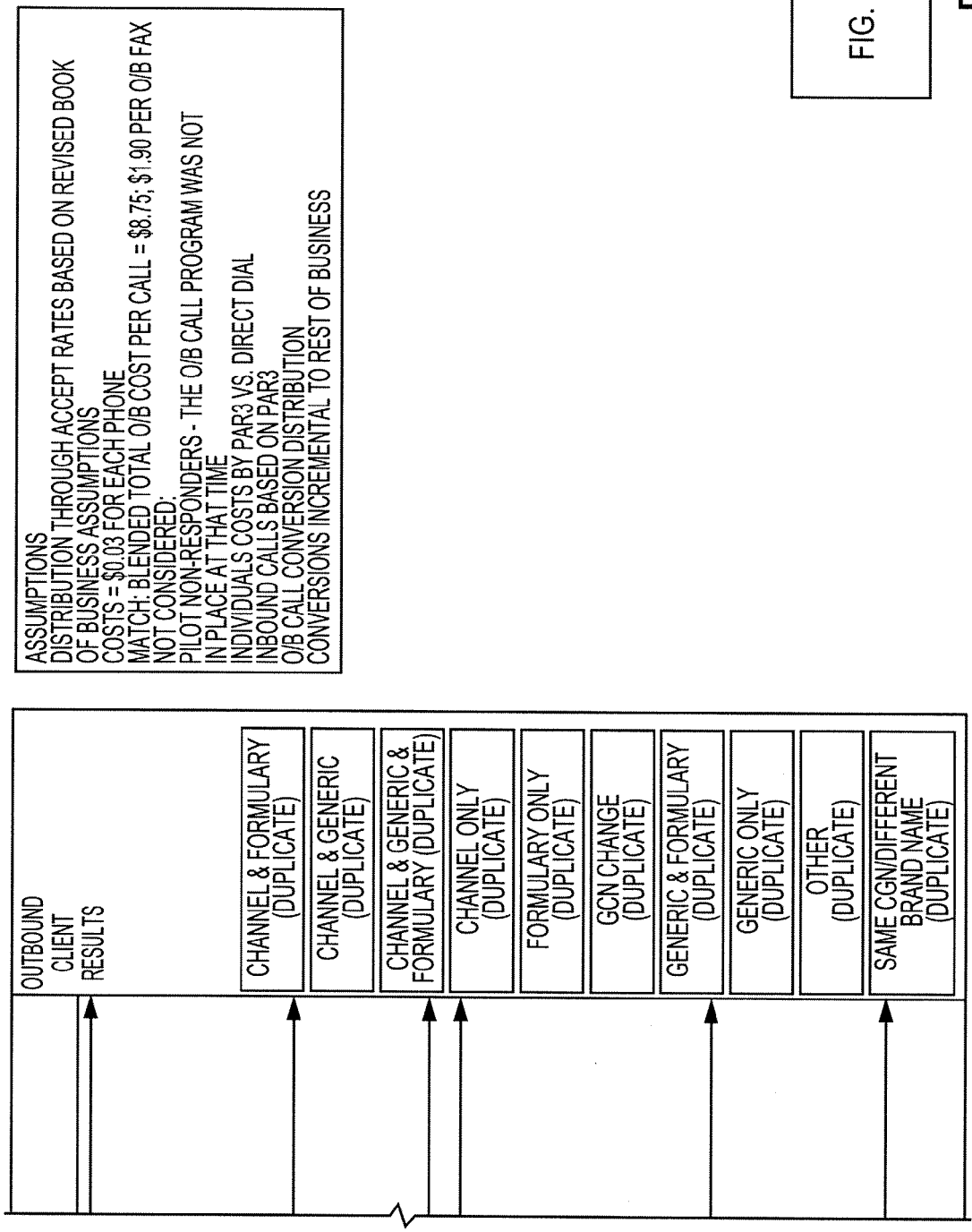

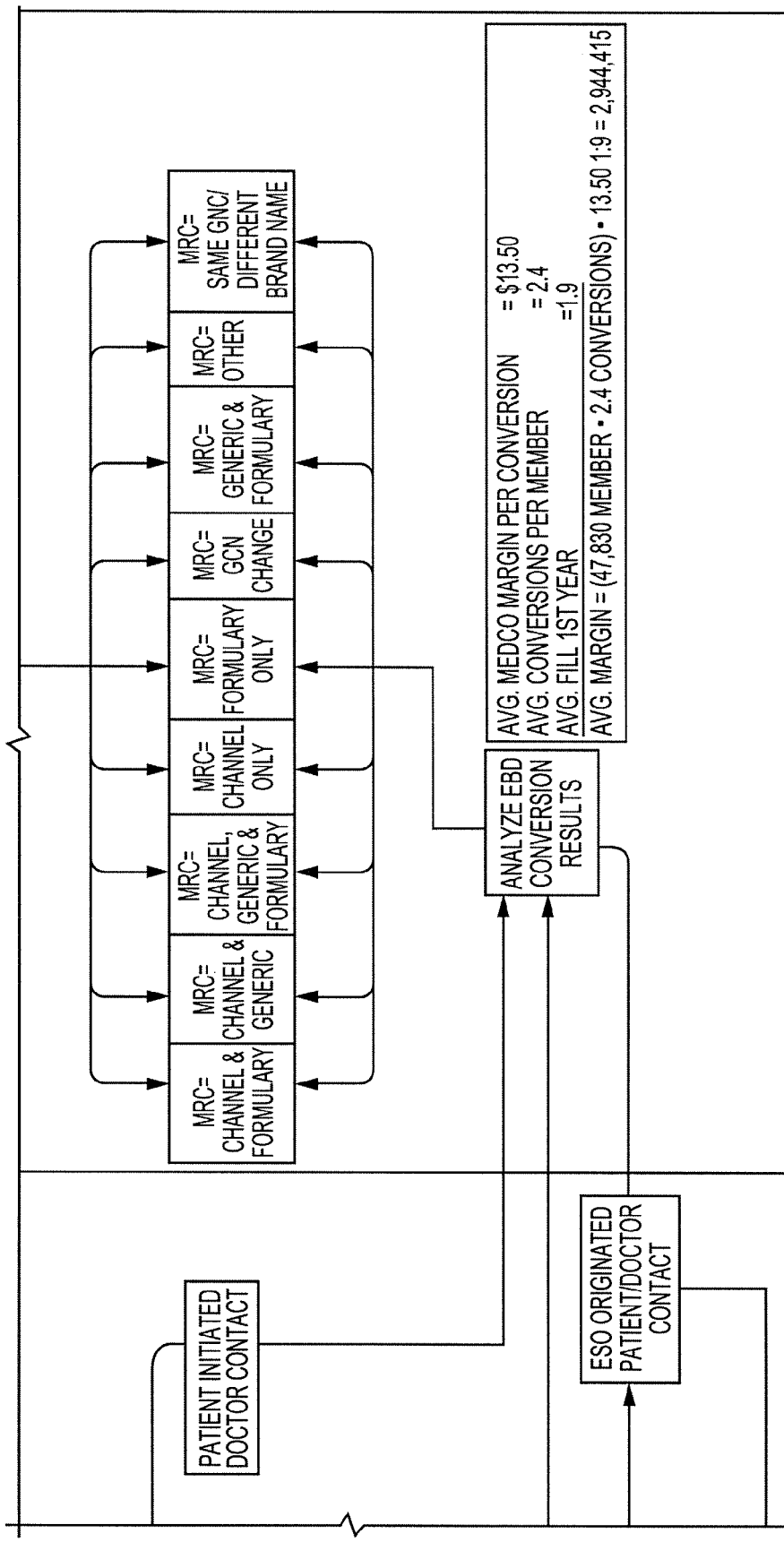
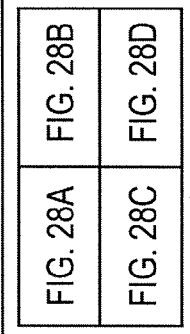
FIG. 28D
FIG. 28

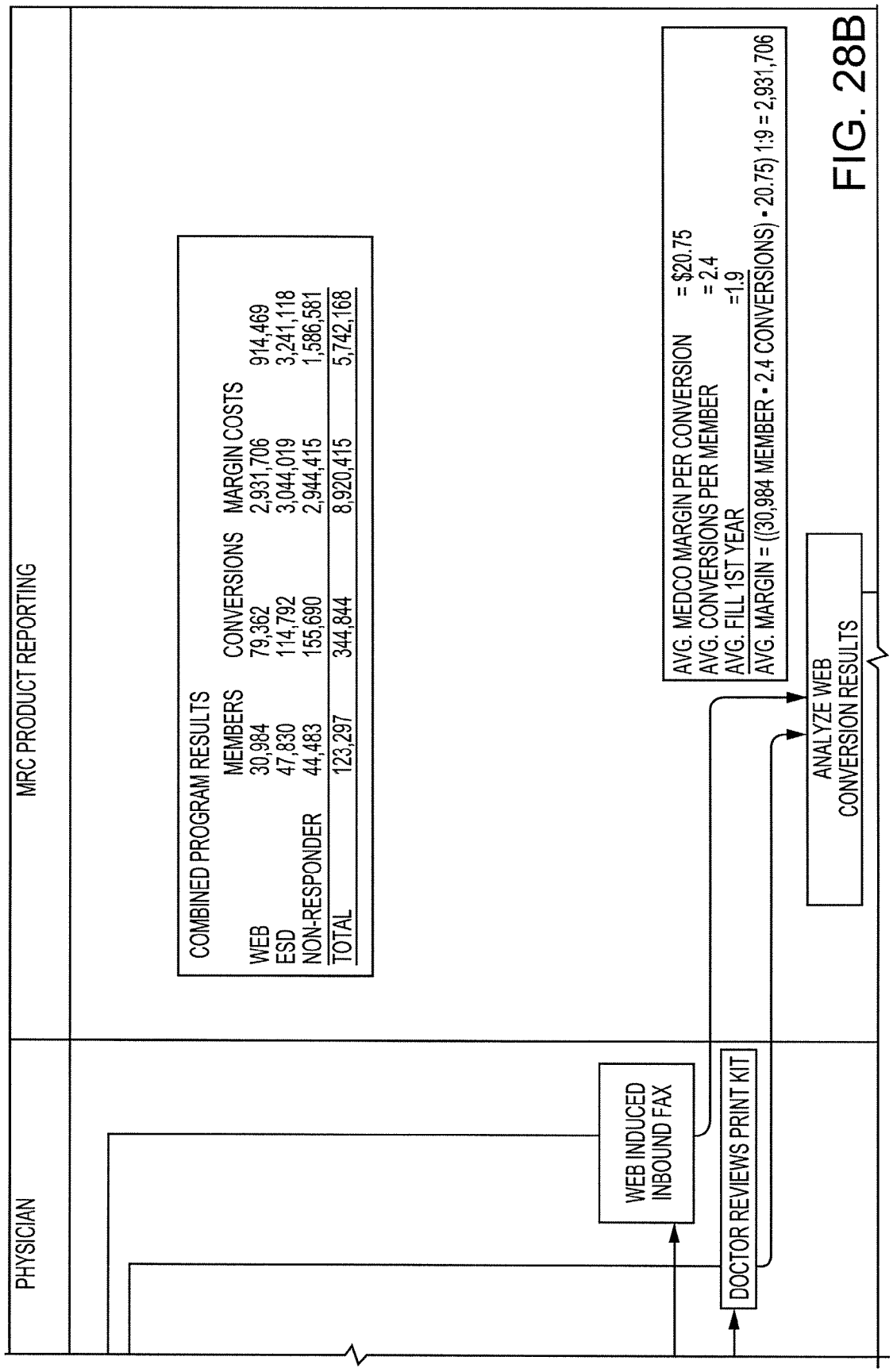

COMPUTER IMPLEMENTED METHOD AND SYSTEM FOR ANALYZING PHARMACEUTICAL BENEFIT PLANS AND FOR PROVIDING MEMBER SPECIFIC ADVICE, OPTIONALLY INCLUDING LOWER COST PHARMACEUTICAL ALTERNATIVES

CROSS-REFERENCE TO RELATED APPLICATIONS

This application claims the benefit under 35 U.S.C. 119(e) of U.S. Provisional Patent Application No. 60/802,196, filed on May 20, 2006 entitled "METHOD AND SYSTEM FOR ANALYZING OF PHARMACEUTICAL BENEFIT PLANS", which is hereby incorporated by reference herein in its entirety.

BACKGROUND OF THE INVENTION

1. Field of the Invention

The invention relates generally to analysis of pharmaceutical benefit plans for determining, for example, whether a specific pharmaceutical benefit plan is suitable for a member thereof and/or for providing the member specific information to make informed decisions with respect to the pharmaceutical benefit plan. In addition, the invention relates more specifically, to providing information with respect to alternative pharmaceutical treatments, including recommending lower cost alternatives for mediations, when appropriate.

2. Description of the Related Art

Pharmaceutical benefit plans are a component of many health insurance plans. They offer coverage (payment) for medications that are prescribed for a wide variety of conditions. Pharmaceutical benefits plans are not standardized, and vary in the coverage and additional costs that patients are expected to pay. Additionally pharmaceutical benefit plans are becoming increasingly complicated and detailed. In this application, the term medication will be used to describe all medications that are recommended and/or prescribed by a doctor for a patient, including biologics, brand name drugs, generic drugs, and over the counter drugs.

Typical features of various pharmaceutical benefit plans include co-payments for every purchase or refill of a medication, coverage for certain medications at only a percentage of cost, no-coverage for other medications, or benefit caps. Additional features may be limitations on the number of re-fills or for long term use of a medication. To reduce costs for an insurer, many pharmaceutical benefit plans do not cover more expensive patented medications when generic or non-patented medications that are therapeutically equivalent or substitutable. Generic medications are non-patented medications identical to medications that were previously patented, and are usually available at substantially reduced costs. Therapeutically equivalent medications may not be identical, but may treat the same disease in a very similar manner, for example, statins used for treating high cholesterol. Multiple statins exist that can treat the condition, and the are therapeutically equivalent, but not identical. Over the counter medications are medication that are approved for purchase without a prescription, they can be patented or unpatented. However, we have determined that members are not able to access the necessary information to make informed decisions. In addition, we have determined that pharmaceutical benefit plan members are not able to control what types of medications to take (or not take) that might be appropriate for their specific condition. Further, we have determined that members are not able to make independent decisions based on best practices and/or medical information.

What is needed is a way of obtaining and/or purchasing medications that will treat a patient's conditions, but in way that reduces costs in view of a patient's pharmacy benefit plan. In addition, we have determined that what is needed is a system and computer implemented method that empowers pharmaceutical benefit plan members to make informed decisions on whether and what medications may be appropriate for their health conditions, in a manner that reduces overall costs.

SUMMARY OF THE INVENTION

One embodiment of the invention describes a method for reducing medication purchasing costs for a member of a pharmaceutical benefits plan. The process includes analyzing a medication prescribed to the member, recommending at least one substitute medication for the analyzed medication, wherein the recommendation is based on the member's pharmacy benefit plan. Receiving, from the member, at least one of an authorization and selection of a substitute medication from the at least one recommended medication, requesting approval from at least one of an authorizing physician, a pharmacist and an authorizing health care professional for the selected substitute medication. This request is grouped together with a plurality of other medication substitution requests. The response to the request for approval is processed to complete the substitution of the medication for the patient, and informing the patient that the substitute medication was approved for at least one of purchase and acquisition.

Another embodiment of the invention describes a computer implemented system for reducing medication purchasing costs for a member of a pharmaceutical benefits plan. The system has a medication analysis engine executing on a computer analyzing a medication prescribed to the member. The system also has a plurality of databases connected to the medication analysis engine, including at least a client profile database comprising pharmaceutical benefits plan information for members recommending at least one substitute medication for the analyzed medication. The recommendation is based on the client profile database and a member's pharmaceutical benefits plan, and the recommendation is also based on known medication substitutions. The medication analysis engine receives from a client interface, operated by the member, an authorization and selection of a substitute medication for the at least one recommended medication. The medication analysis engine also requests approval from at least one of an authorizing physician, a pharmacist, and an authorizing health care professional, for the selected substitute medication. The approval request has the requested approval and a plurality of other medication substitution requests, grouped together on the approval request. The medication analysis engine processes the response to the requested approval to complete the substitution of the medication for the patient, and the result is shown on an interface, informing the member that the substitute medication was approved for at least one of their purchase and acquisition.

Another embodiment of the invention describes a method for reducing medication purchasing costs for a member of a pharmaceutical benefits plan including, requesting a medication to be analyzed from a member, analyzing the medication requested by the member, recommending at least one substitute medication for the analyzed medication, wherein the recommendation is based on a database of known medication substitutes, receiving, from the member, at least one of an authorization and selection of a substitute medication for the at least one recommended medication, requesting approval from at least one of an authorizing physician, a pharmacist and an authorizing health care professional, for the selected substitute medication, grouping the requested approval with a plurality of other medication substitution requests, processing the response to the requested approval to complete the substitution of the medication for the patient; and informing the patient that the substitute medication was approved for at least one of purchase and acquisition. In another embodiment, the authorization and selection of a substitute medication from the member can be based on dose and strength to provide an accurate and actionable alternative.

Another embodiment of the invention describes a method for reducing medication purchasing costs for a member of a pharmaceutical benefits plan using a wireless mobile computing device. This method includes receiving a request to analyze a medication from a patient using the wireless mobile computer device, analyzing the medication requested by the member, recommending at least one substitute medication for the analyzed medication, wherein the recommendation is based on the member's pharmaceutical benefits plan, receiving, from the member, at least one of an authorization and selection of a substitute medication for the at least one recommended medication, requesting approval from at least one of an authorizing physician, a pharmacist and an authorizing health care professional, for the selected substitute medication, grouping the requested approval with a plurality of other medication substitution requests, processing the response to the requested approval to complete the substitution of the medication for the patient, and informing the patient, through the interface of the wireless mobile computing device, that the substitute medication was approved for at least on of their purchase and acquisition.

BRIEF DESCRIPTION OF THE DRAWINGS

Various objects, features, and advantages of the present invention can be more fully appreciated with reference to the following detailed description of the invention when considered in connection with the following drawings, in which like reference numerals identify like elements.

FIG. 7 shows an interface allowing a patient to enroll in the savings program.

FIG. 8 shows additional information that may be included in plan enrollment.

FIG. 9 shows an interface allowing a patient to have an analysis done on the medications they are currently taking.

FIG. 12 shows an interface allowing a member to select a substitute medication.

FIG. 13 shows an alternative interface allowing a member to select a substitute medication.

FIG. 14 shows an interface informing the member about getting a doctor's approval for the substitution of a medication.

FIG. 15 shows an interface allowing a member to confirm their request for approval to a doctor.

FIG. 16 shows an interface used by a doctor to approve substitutions.

DETAILED DESCRIPTION OF EMBODIMENTS OF THE INVENTION

Figure 1:
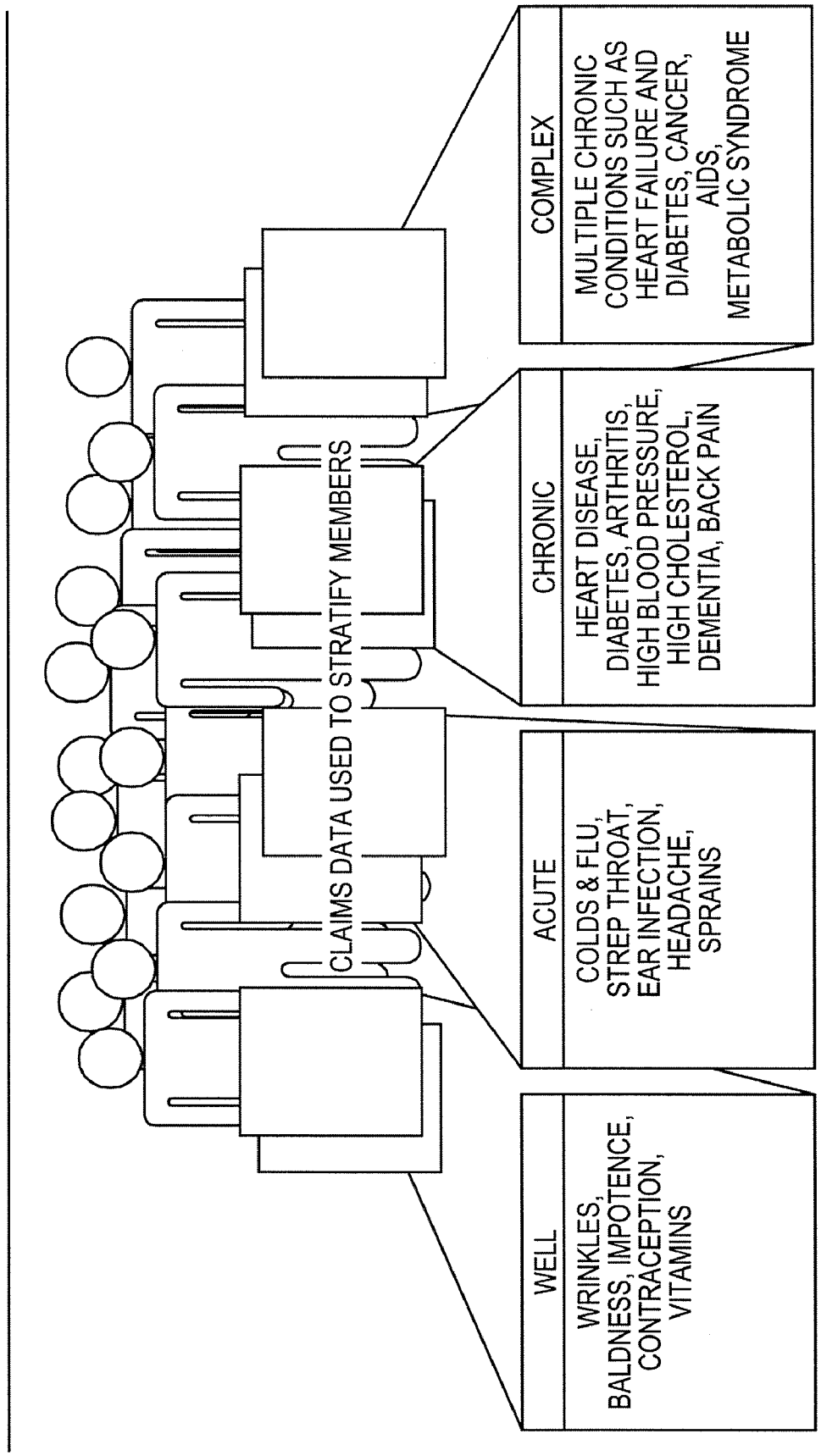
FIG. 1 shows how patients can be stratified into different groups based on the condition of their health.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention.

In addition, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

Embodiments of the invention relate to methods and system for analyzing pharmaceutical benefit plans to determine whether a patient, member, household, group, or client is efficiently participating in and taking advantage of the coverage and benefits included in their pharmaceutical benefit plan. The analysis results in one or more recommendations of alternative medications along with the savings a member could expect by switching to the recommended medications.

These recommendations are offered to the member, and their selections are sent for approval to the prescribing doctor. The doctor, can approve, deny, or request an in person visit with the patient.

In some embodiments of the invention, the request for approval of the member's selection may be electronically forwarded to the member's prescribing physician, with the request being grouped (bundled) with other member selections. The results of the physician's decisions may be electronically received by the system and reported by the plan manager to the member for review.

The system analyzes prescription plan enrollment data, eligibility, prescription claims, prescribing physicians, and other member profile data to generate alternatives for the medications in a patient's claim history. The alternatives may include medications within the same and related classes based upon National Drug Codes, formulary alternatives, alternative cost savings, etc. Along with the alternatives, the member can be presented with the costs savings, including the member's payment (i.e. "you pay") for either retail or purchase by mail. In some embodiments of the invention, the member may be provided with several alternatives regarding the selection of "low cost generic medications". Embodiments of the invention also allow the purchasing of "multiple months supply" of medications via mail service dispensing. In some embodiments, the recommended medication may not be less expensive, but may be more effective, less likely to cause harmful interactions, or have fewer side effects. In other embodiments, the alternative medication may be an over the counter drug that is not covered by a pharmaceutical benefits plan at all.

The system can also be designed to be proactive and automatically notify a member when cost saving alternative medications are available. A member's claim history can be analyzed proactively to determine if any savings opportunities are available, and the member can then be mailed or emailed information about the savings opportunities. This pro-active analysis can be combined with patient stratification techniques to identify the members that could benefit most from substitution of medications. After receiving the mailing or email, the member can respond using any of the embodiments of the invention, including logging into the online My Rx Choices, responding through mail, or using a mobile phone or other internet enabled mobile device.

In some embodiments of the invention analysis can be done on an individual's current or planned prescriptions even when they are not a member of a particular pharmaceutical benefits plan. Information about the individual's prescriptions can be collected and used to provide substitute medications that will likely result in a potential cost savings. Without specific information about the individuals pharmacy benefit plan, a final cost savings cannot be determined. However, such a system can still be useful for marketing purposes, or informational purposes for individuals that might not otherwise be aware of alternatives. Alternatively, the substitute medication may be more effective even if they are not less expensive.

Embodiments of the invention can be implemented using a client server system that coordinates communication and activities between the member, a doctor, and the drug manufacturer. The client server system can be implemented using an Internet connected client computer with a web browser. A browser can be used to run a web application running on the server. The client server system can also be implemented using a mobile phone, or other mobile computing device that is Internet connected, and capable of running a full blown or limited web browser. Alternatively, a specially designed application can be deployed on the computer or mobile device, along with a corresponding server application on the server to implement the client server system. Other embodiments can include use of the mail, an automated voice response system by phone, or use of short messaging system (SMS) from a mobile device.

FIG. 1 shows how patients can be stratified into different groups based on the condition of their health. Patients can be well, meaning that they are healthy, but might have some common and normal issues such as wrinkles or baldness. Patients can also be acutely sick, meaning that they have an illness that is otherwise treatable or will improve with time. Common examples of acute sickness are the flu, or a sprain. Patients can also be chronically sick, these are health conditions that are not curable, but can be treated and managed. Finally, patients can be grouped into a category called "complex" for those health conditions that are more unusual or difficult to treat, or the result of multiple other health conditions (e.g. cancer). Patient stratification is important to understanding a patient's medication usage. Patient stratification results may be available for transmittal to and storage in Patient-On-Line Authoritative Record (POLAR). Patient stratifications comprises a number of well known techniques known to one of ordinary skill, that can be used in conjunction with the present invention.

Figure 2:
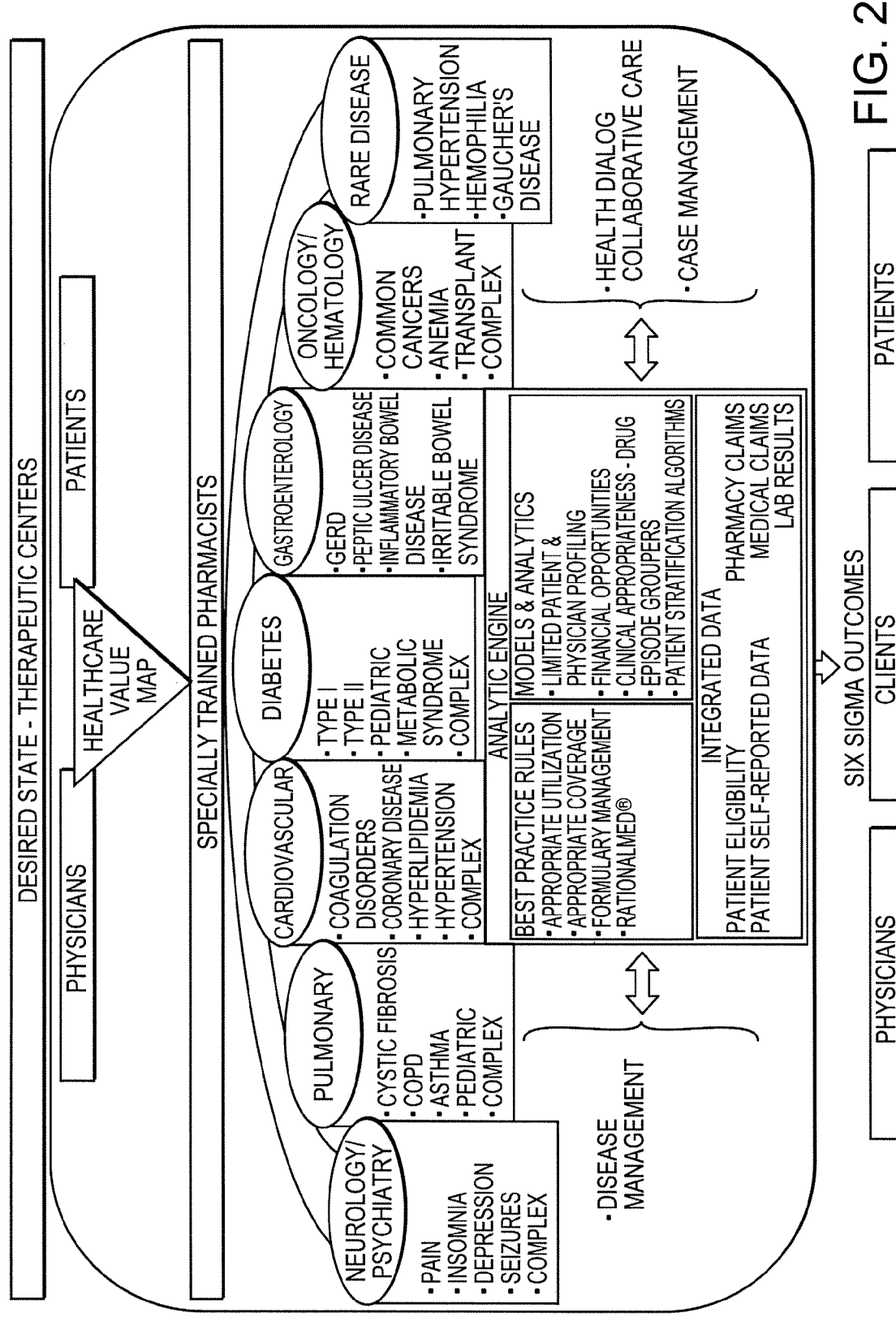
FIG. 2 shows the benefit manager in the context of the health care delivery system.

FIG. 2 shows how the My Rx Choices fits into the context of the health care delivery system. The analytic engine making up the My Rx Choices connects doctors, patients, and pharmacists. The analytic engine combines information from many areas of medicine, including information about drug interactions. The analytic information also combines disease management information and case management. With this background of information, along with formulary information, and other best practices, an analysis can be done to determine what medications can be substituted for a patient. The analysis can be done using a variety of methods including patient profiling, consideration of financial costs, clinical appropriateness, and patient stratification, as described below in detail.

Figure 3:
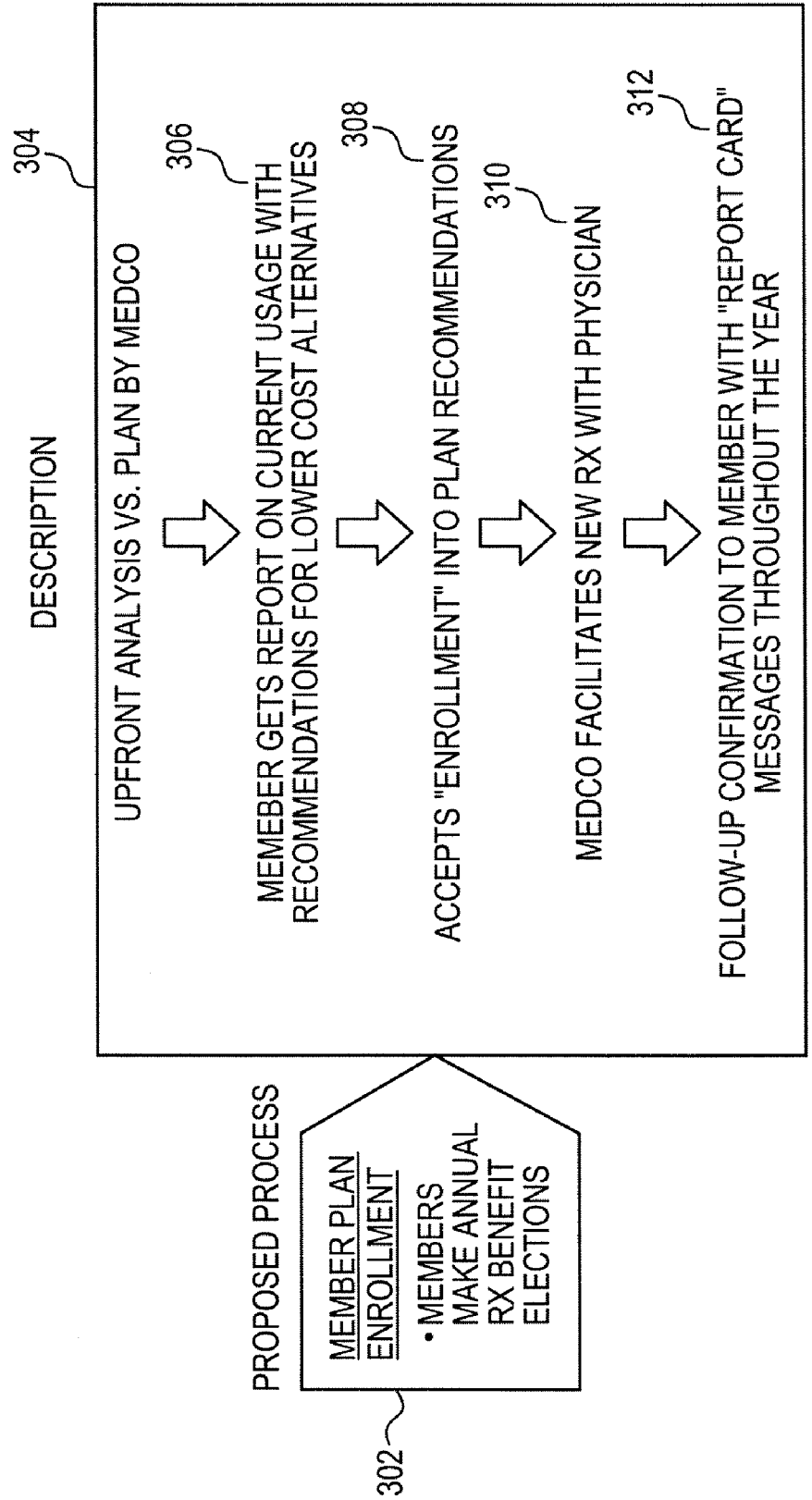
FIG. 3 shows an overall flow diagram explaining operation of the invention.

FIG. 3 shows an overall flow diagram explaining the overall operation of the system in accordance with at least one embodiment of the My Rx Choices of the present invention. The process includes, for example, enrolling a patient, analyzing their current prescriptions, suggesting alternative medications, getting them approved, and reporting the savings to the patient.

The first step 302 is that a member enrolls in the program (See FIGS. 7 and 8 and related discussion). Enrollment consists of entering in a member's information (or confirming an identity for previously stored information). At step 304, an analysis is done of the member's current prescriptions (See FIGS. 5 and 10 and related discussion). This analysis can be done automatically for some or all of the member's prescriptions, or it can be done at the member's request. At step 306, a reported is generated from the analysis and shown to the member. The report shows medications for which lower cost alternatives are available. The member can select between these presented alternatives (See FIGS. 12 and 13 and related discussion). A member can also decide not to change any prescriptions. At step 308, the enrollment process is completed once the patient has entered their prescription information and selected alternative medications. The enrollment process can also be limited to just patient information, with any analysis to be done at a later time. At step 310, the My Rx Choices facilitates receiving approval from a doctor for the substitution (See FIG. 15 and related discussion). At step 312, a confirmation is shown to the user, and "report card" updates are sent throughout the year. The "report card" updates can be sent at any interval, or may be omitted entirely in some embodiments of the invention.

Figure 4:
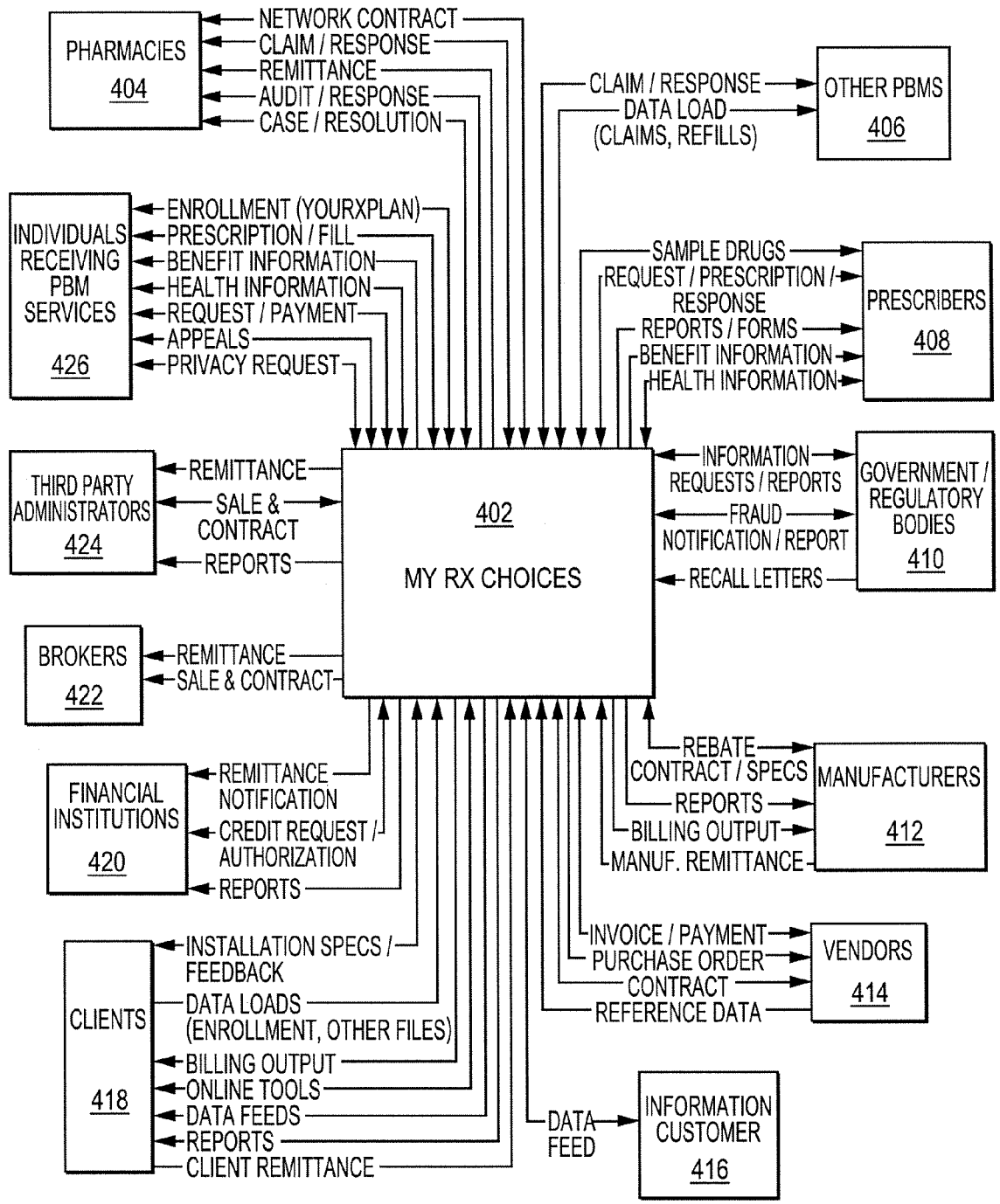
FIG. 4 shows an overall system diagram of how the benefit manager interacts with other parties in the delivery of health care.

FIG. 4 shows an overall system diagram in accordance with at least one embodiment of how the My Rx Choices interacts with other parties in the delivery of health care. In the center of the diagram is the My Rx Choices 402, it coordinates activities and information between the other parties involved in providing medications to patient. The saving manager coordinates activities between prescribers 408, pharmacies 404, and individuals 426 to implement the delivery of alternative medications to a patient.

The operation of My Rx Choices 402 is governed by various government and regulatory bodies 410 such as the Food and Drug Administration. These regulatory bodies have laws and regulations covering all aspect of a pharmacy benefit manager's (PBM) operation. For example, privacy regulations such as the "Health Insurance Portability And Accountability Act" regulate the use and disclosure of personal information. The regulatory bodies 410 can interact with the activities of the My Rx Choices 402 through information requests or reports, fraud notification or investigations, and recall letters. The operation of My Rx Choices is designed to be in compliance with these laws and regulations.

My Rx Choices 402 also interacts with manufacturers 412. Manufactures make the medications that are eventually sold to customers. Sales data collected by My Rx Choices can advantageously be sent to manufacturers to assist their operations. Manufacturers can send rebates and other manufacturer remittances to My Rx Choices 402 in accordance with agreements between the parties.

My Rx Choices 402 also interacts with vendor 414. Vendors provide service and information to My Rx Choices. For example, one vendor is Rxaminer who can provide the alternative medications and content used by My Rx Choices.

My Rx Choices also interacts with information customers 416. These are customers of the information that is collected by My Rx Choices from many different sources. These sources can be patient purchases, doctor's prescriptions, and rebate usage. Information customers can be insurers or other businesses interested in information about prescription medications used.

My Rx Choices also interacts with clients 418. These clients are insurers that are using the services of My Rx Choices 402 to reduce insurance costs. My Rx Choices sends information like installation information and reporting. This allows client to know how My Rx Choices is helping its customers. My Rx Choices also sends data about prescriptions and purchases by patients so that client can use them for insurance and billing. This way insurer can quickly and easily be notified of the costs incurred by its patients.

From the client 418, My Rx Choices 402 receives patient data such as profile and health information. This data can be used to simplify and reduce errors in the enrollment process, because otherwise a patient would need to reenter all their personal information and other health history. Clients can also send feedback and other reports to My Rx Choices to help improve its operation and understand customer's wants and needs.

My Rx Choices 402 also interacts with financing institutions 420. These institutions are involved in payment processing and transferring of funds. Integration of these functions with My Rx Choices 402 allows patients to easily pay for the medications they have switched to. Patients can pay using cash, credit, debit, check, or other well known payment methods. For example, these financial institutions 402 can be credit processing companies for providing credit authorization service, or banks for completing debit transactions.

My Rx Choices 402 also interacts with brokers 422. Brokers 422 are resellers of PBM services which include access to systems like My Rx Choices.

My Rx Choices 402 also interacts with third party administrators 424. These administrators are responsible for helping patients understand and enroll in their pharmacy benefit plans. For example, they may be employees of insurers or the employers of patients.

My Rx Choices 402 also interacts with individuals 426. Individuals interact with My Rx Choices to enroll in the program, fill prescriptions, review benefit information, and review health information. Individuals also use My Rx Choices 402 to substitute alternative lower cost medications. From individuals, My Rx Choices 402 receives information on prescriptions they have purchased, health and other survey information, and payment information.

My Rx Choices also interacts with pharmacies 404. The pharmacies contract for the services of My Rx Choices 402. Pharmacies 404 send claim information and case information to My Rx Choices. Savings manger 402 provides pharmacies with remittances and audit information.

My Rx Choices also interacts with other PBMs 406. Information about claims and other data (e.g. patient data) is transferred between cooperating PBMs like My Rx Choices 402. Using this information, a coherent and complete set of information can be presented to the patient even though certain medication purchases were made outside of a particular My Rx Choices's network. This network of partners may include non-contracting pharmacies or insurers.

Overall, My Rx Choices is involved in a large number of complex interactions between one or more of the parties described above. Each party needs certain information to perform it tasks. By exchanging information with My Rx Choices of the present invention, the needed information can be obtained, and by providing information to My Rx Choices, other parties can be notified of the information they need to complete their tasks.

Figure 5:
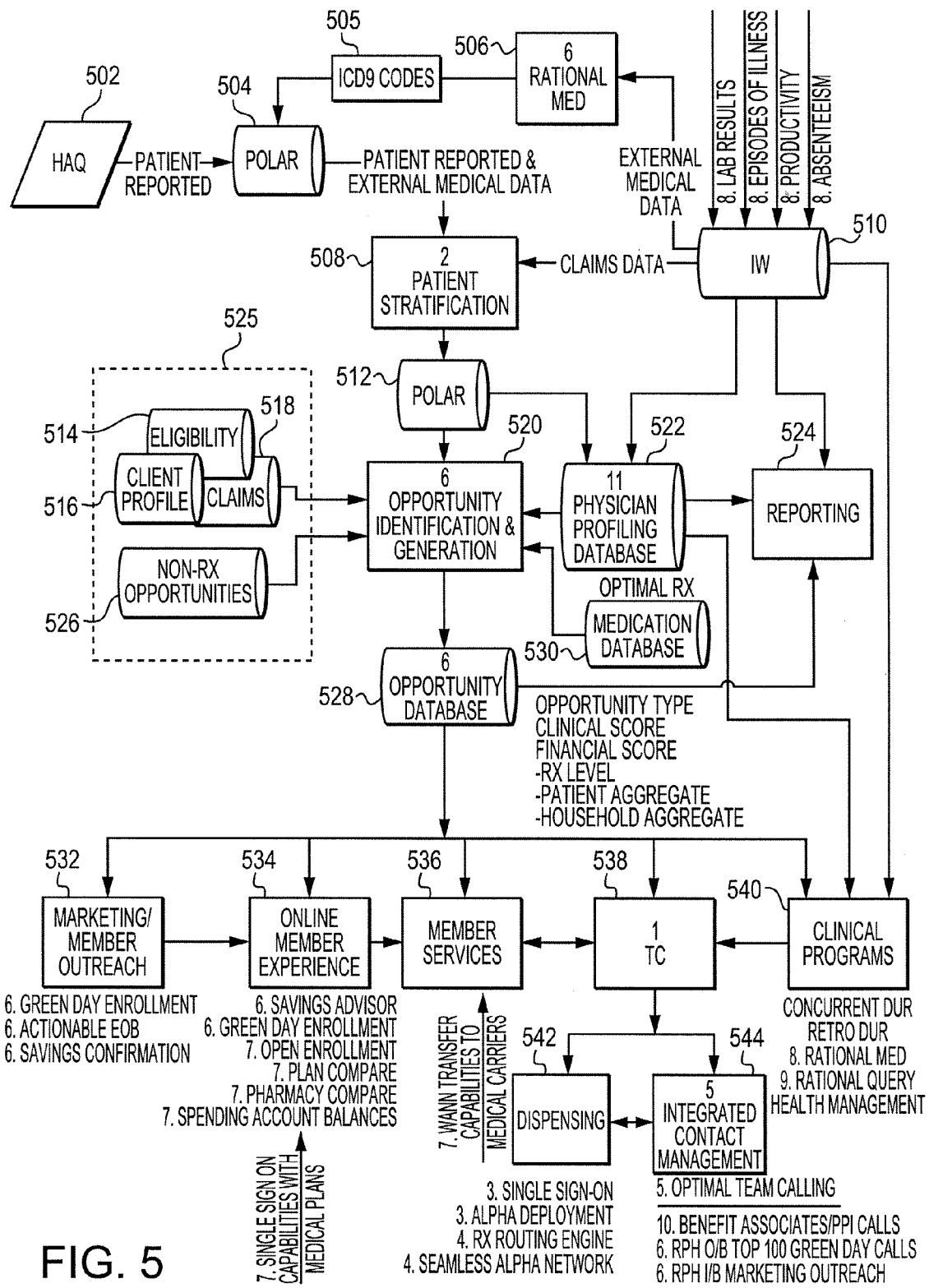
FIG. 5 shows an overall system diagram of the benefit manager.

FIG. 5 shows an overall system diagram of My Rx Choices 402 in accordance with at least one embodiment. The My Rx Choices is made up of a number of databases such as one or more of the following: patient information, claim information, medication information, and doctor information. This information is analyzed in a cohesive manner, and the results are reported to the patient and optionally the physician, pharmacist and/or the pharmaceutical benefits plan.

IW 510 can be utilized to provide clinical and financial business information by analyzing claims data and medical history. The data in IW 510 can also enable benefit plan managers to perform key analysis and client reporting. The IW is a data repository that supports clinical and financial analysis, both patient and client centric, as well as reporting claims activity.

Information warehouse (IW) 510 is a database that stores a history of patient medical records and adjudicated, prescription claim information. The database is continually updated with new information, although it also contains historical information. It may contain patient information and previous medical records, and prescription claims that have been compiled over a period of time. The medical records can include, prescription plan information, claims history, home delivery purchases, retail purchases, refill history, prescription costs, co-pay history, lab results, and episodes of illness. The information warehouse is designed to be suitable for utilization with Health, Allergy, & Medication Questionnaire (HAQ) 502. The IW can also be used with the International Statistical Classification of Diseases (ICD) 505 data to analyze patient stratification.

Patient stratification is a result of proactively analyzing member prescriptions. Savings opportunities and customized communications are then sent to the member based on the amount of money they can save and how they were classified. Patients with the most savings get more detailed information to encourage them to use a system like My Rx Choices. Further, this stratification can be used when running and outbound calling campaign to spend resource calling those members who could benefit the most for change to alternative medications.

Incorporated into the IW 510 can be standard third-party data software to identify an individual across the book of business, and not only within a particular client database. The process assigns each person a unique member identifier, regardless of whether members are eligible, in multiple groups, or have had interrupted coverage. This capability, along with the capability of analyzing behaviors over time, makes the IW 510 an optimum source of data collection and analysis for utilization with the present invention.

The IW 510 can use an agent to collect data from production systems to be included in the IW. In one embodiment, the production systems reside on an IBM mainframe and the IW on a Teradata database. On a cyclical basis, data is loaded to the Information Warehouse and made available for other reporting applications. In addition to the data collection activities, data cleansing, balancing, and formatting takes place.

In greater detail, in one embodiment the IW 510 is composed of nearly 463 entities of which 327 are code tables and over 10,000 data elements. An Online Data Dictionary is an electronic reference source that can be used for documenting the contents of the Information Warehouse. Its objective is to help in understanding how the information in the Information Warehouse is organized, what it means and how specific items can be found.

The Information Warehouse may be viewed from both a physical and business perspective. From a physical perspective, data in the IW 510 is organized in a relational database structure. Each table pertains to a specific category of information, such as claim or client. Each row is a collection of information relating to a single instance of whatever it is the table describes (e.g. single claim, individual client). Each column pertains to a specific piece of information, such as a claim number or client name. Each column also has a number of attributes, such as data type, that defines what kind of data is permissible (e.g. number, date, text string). The Online Data Dictionary addresses the physical organization of the Information Warehouse and displays many of the important physical aspects of the data via a database browser screen.

From a business perspective, each table in the Information Warehouse conceptually belongs to a specific subject area (i.e., Claim, Drug, Patient, Client, Provider, etc.). The Online Data Dictionary provides table and column descriptions which define their business meaning and usage. The Online Data Dictionary also has keyword and flexible search capabilities to quickly locate specific information and provide answers to frequently asked questions.

The IW is organized into several major categories, called "subject areas." This facilitates user access to and analysis of the information in the subject areas. The Claim Subject Area may be thought of as the central category, with the other subject areas providing reference information to help understand a claim. The Claim Subject Area contains facts about the claims submitted by members of clients in conjunction with the dispensing of medical products. The main data category within this subject area can be a set of 9 physical claim tables, organized by client, which house the claim data. Each claim has relationships to the reference data in each of the other Subject Areas. For example, a claim will point to the relevant prescriber in the Provider Subject Area table(s). Similarly, a claim will point to the relevant product, group and member in the Drug, Client and Patient Subject Areas, respectively. As a result, the amount of reference data kept in the central fact table is reduced. This subject area includes numerous attributes related to the claim type, prescription, pricing, dispensing, refills, cost components, adjudication, adjustments, copay, deductible, etc.

The Client Subject Area contains reference data about the client organizations that currently use or recently used the services of the pharmacy benefit management. The main data categories within this subject area are the multi-level operational units comprising a client organization (client organizational ids, carriers, contracts, groups, benefit groups and related groups) and the high-level products and services that a client has contracted for (e.g. disease management programs). Each type of relationship that links the different client operational levels is shown as a separate hierarchy (e.g. client sales hierarchy, client billing hierarchy, etc.). This subject area includes various attributes that characterize a client's status, organizational classification, eligibility rules and special processing requirements. It also identifies the claim table where a client's claims are maintained.

The Drug Subject Area contains reference data pertaining to pharmaceutical and other products that have been approved for sale by the Food and Drug Administration (FDA). The main data categories within this subject area are the medical products from manufacturers, product pricing and formularies, and their organization into therapeutic chapters and sub-chapters. Medical products include both drugs and certain non-drug products, such as medical supplies. A drug product has numerous physical attributes, such as strength, dosage form, administration route and package size. A drug product also has identification attributes, such as numeric codes and names. Drugs are classified according to criteria that reflect the generic formulation, generic market status and therapeutic class. This subject area includes the classification of drugs, their therapeutic properties and uses, and the classification of diseases and medical conditions.

The Patient Subject Area contains reference data about the active and retired employees of clients who receive pharmacy benefits. The main categories within this subject area are memberships, members, and patients. Membership identifies the members covered under a particular benefit plan. A member is an individual covered under a membership, including the originating subscriber and any dependents to which benefits have been assigned. This subject area includes membership and member identifiers, coverage attributes and member attribute data. It also identifies a member's primary care provider and members within each carrier for whom claims have been submitted.

The Provider Subject Area contains reference data about the individual practitioners and provider organizations involved in providing health care services such as writing prescriptions for and dispensing drugs. The main data categories within this subject area are the individual practitioners authorized to write prescriptions (also known as "prescribers") and the pharmacies that process and fill the prescriptions. Practitioners may be classified by type of medical practice and medical specialty. Provider organizations may be classified by type of pharmacy, organizational status (pharmacy or pharmacy organization) and organizational affiliation (chain, franchise or unaffiliated). This subject area includes the various identifiers used to identify providers, as well as provider attribute data, some common to both pharmacies and practitioners, such as name and address, and some specific to one type or the other.

HAQ 502 is a survey provided to individual patients for the reporting of drug allergies, medical conditions, adverse effects to medications, and other information that will aid a prescription writer (e.g. doctor) or pharmacist to determine whether a particular medication is suitable for the patient. This information may be utilized to perform a standard Clinical Drug Utilization Review (CDUR) to check for potential drug reactions before filling a prescription or recommending a medication interchange. Clinical information on the completed form is reviewed and coded to align with CDUR standard rules and associated coding. The HAQ information received from the patient may be coded and relayed to Patient Stratification 508 and Client Profile 516. The process to collect and make use of an individual's drug allergy and medical conditions is called solicitation and resolicitation. Solicitation and periodic resolicitation is a business requirement and mandatory under Pharmacy Practice Standards and state regulations. The HAQ can be solicited in multiple ways including standard mail processes, telephonically in customer service, and electronically (e.g. a web interface).

Patient stratification algorithms 508 are also incorporated into the My Rx Choices 402. Patient stratification is a method of computer analyses of medical records, disease and prescription claim information contained in the HAQ 502, ICD 505, and IW 510 to determine the potential benefit from applying the system and methods of the invention to a patient's prescription information. If sufficient medical record and prescription claim information is available to perform a patient analysis, the patient may be stratified into one or more wellness categories, e.g. well, acute, chronic, complex, etc. Each wellness category may be further defined, for example, by the past medications prescribed to a patient, illnesses, and diseases states. See FIG. 1 for further details. Patient Stratification results may be available for transmittal to and storage in Patient-On-Line Authoritative Record (POLAR) 504.

The International Statistical Classification of Diseases (ICD codes) 505 provides a detailed description of known diseases and injuries and is published by the World Health Organization for use in recording morbidity and morality, reimbursement systems, and automated decision support in medicine. For example, the ICD9 denotes the 9th Edition of the Codes. Every disease (or group of related diseases) is described with its diagnosis and given a unique code up to five letters long. A database of ICD Codes is provided to POLAR 504 and may be routinely updated as the data changes. ICD Codes may be coded into the database and made available for use in Patient stratification 508 analysis, as well as other components of the system.

Patient On-Line Authoritative Record 504 (POLAR) is a standard on-line system that links and stores data at a person-level. Alternative commercially available systems to POLAR may also be used. The database houses multiple sources of demographic data, clinical (medical and drug allergy) information, e-mail addresses, preferences, mandatory communication tracking, and levels of consent and authorization required to meet Privacy and Security regulations. The information is collected and stored from a variety of internal and external sources. Data may be compiled and assimilated from self-reported information, eligibility information, customer service records, data providers, home service delivery operations, E-commerce sources, and other data sources. Data points can be date/time stamped and follow the person throughout their relationship with a pharmacy benefit manager. One method of following a patient is to assign a unique identifier to each patient, for example an artificially generated number (AGN).

Some standard features of the POLAR database system are a real-time person-centric view of an individual's data, including, demographic Information, geographic Information, medical conditions and drug Allergies, preferences, e-Mail addresses, mandatory Communication Tracking, HIPAA Privacy Consent and Authorizations. POLAR represents the single and authoritative source of an individual's data across the entire PBM's enterprise. POLAR 504 also allows individuals to be rolled up into a membership or family unit. POLAR has a wide variety of software applications with the core objective to increase data quality and content for clinical data used by DUR, Home Delivery Pharmacies, Customer Service, and Internet applications.

POLAR stores current and historic preference information for individuals in its databases. Currently, however, preference information is limited to an individual's desire to either Opt-Out or Opt-In to a product or service, Refill Reminder and Never Ask preferences, as well as E-Health preferences. The present invention advantageously provides enhanced functionality and processes described herein that is used in conjunction with POLAR to provide new functionality and empower individuals to control their usage of medications under the pharmaceutical benefits plan.

POLAR includes a management tool call the Data Quality Dashboard, which is a secure tool that permits approved users to view selected data fields using aggregate descriptive statistics, selected defined metrics and/or graphical representation of metrics. This reporting capability provides end users with summary information about the POLAR data stores. This system is implemented as a collection of batch mainframe programs and BRIO on-line reports. This application system provides users with graphical views of the quality of specific demographic and clinical data within the POLAR data stores.

Additional features that can be incorporated into POLAR include a permissions and restrictions management system that would manage the storage and access of consents and authorizations for members.

POLAR 504 receives data from Patient stratification 508 and analyzes it to assign an AGN suitable for routing prescription data to an Opportunity Identification & Generation (OIG) component. The OIG component can provide an analysis of potential opportunities for substituting drugs and thereby generate cost savings for a member of a particular prescription benefit plan.

Physician Profiling Database 522 is a repository of physician (doctor) information gathered from various sources that are generally available to the public. Information within the database includes, name, age, business address, telephone number, pager number, email address, areas of medical practice, hospital association, acceptable insurance plans, referral physician for an insurance plan, household, and group or client information. All this information may be stored and regularly updated in the database for rapid access. Other information in the database may include the history of prescriptions the doctor has written, and the associated prescription claims data based on those prescriptions. This type of information is contained within health management database 525. The prescription history data may be categorized into brand name, generic and over-the-counter medications, within or outside a particular formulary plan.

In some embodiments of the invention, individual doctors, or groups of doctors in a practice, may be assigned an arbitrary score representing the doctor's history of accepting certain insurance coverage, writing prescriptions for brand name drugs, writing prescriptions for generic drugs, recommending over-the counter medications, and approval history for alternative drugs. A lower physician score may generally indicate that a physician is less likely to approve a "pharmacist recommendation" for a medication substitution, and a higher score may generally indicate that a physician is more likely to approve a substitution.

Health management database 525 is formed by databases of eligibility information 514, client profiles 516, claims 518, and non-prescription opportunities 526. The data in these databases can be provided by a medication prescriber (e.g. a doctor). A history of the patient's prescription claims, eligibility and coverage, and client (i.e., insurer) profile may be retrieved from the IW 510. This information can be analyzed by OIG to determine whether the patient's insurance coverage is adequate for substituting a medication prescription. Client profile database 516 can include information such as patient identifiers, patient names, patient addresses, insurance providers, co-pay information, formulary information, and prescription order histories. Non-Rx Opportunities database 526 is a database of alternative medications and actual costs for those medication. This allows patient to also consider non-prescription substitute medications. These over-the-counter medications may or may not be within the patient's formulary, but may be made available for the patient and prescription writer to consider when there is a potential cost savings. After new Health management database information is utilized for current Opportunity & Identification Generation analysis, the raw data along with the analyzed data may be compiled and stored in IW 510 for future use.

Medication database 530 contains listings of all FDA approved brand name drugs, FDA approved generic drugs, as well as over-the-counter medications, along with both retail and wholesale price information. The medications may be categorized by active ingredient, use codes, and/or generic equivalents. The information is frequently updated to provide real time cost and FDA use codes. From the claims history data available in IW 510 and Health management database 525, a particular medication name or use code may be provided to the Medication database to determine possible substitute medications that may provide a cost savings over the currently utilized medication. The substitute medications can then be transmitted to Opportunity Identification & Generation 520 for further analysis.

The help identify substitute medications, the services of a vendor, like Rxaminer, can be used. Rxaminer maintains a rules engine that maps medications to clinical alternatives at the national drug code (NDC) level. A target drug is provided to Rxaminer for analysis, who response with a set of possible alternative medications. The rules engine contains generic equivalents, generic alternatives, brand alternatives, and OTC's. The set of alternative medications from a vendor like Rxaminer are priced using information about a member's specific pharmaceutical benefit plan. The analysis of Rxaminer can be used in conjunction with the information stored in medication database 530.

Opportunity Identification & Generation 520 receives raw and compiled data from the above referenced components of the system, i.e. patient, member, client profile, physician profile, patient stratification, etc., and coordinates with a vendor like Rxaminer to generate potential medication substitutions that will result in cost savings to a plan member. The analysis is based upon established criteria such as patient quality rules along with data from POLAR 504, Physician profiling database 522, Health management database 525, and Medication database 530.

Cost savings can also be generated based on pricing for the medication from specific sources. The system provider may be able to provide the drug at low cost, for example, through the mail. However, other retail pharmacies or mail order pharmacies may be able to provide better prices. Cost savings can be generated and reported to the member for each one of these possible options, allowing the member to select their preferred source, which may be based on personal preferences, service considerations, or other incentives.

In general, analysis for substitute medications can be done for all members of the PBM who request it. In some embodiments, to improve the performance of the system, and to provide more meaningful results, the analysis can be done only for certain members. To determine the eligibility of members, claim history and enrollment applications can be reviewed to find those members that are potentially under utilizing the benefits of a particular prescription coverage plan. Those patients, based upon the current rules, that are deemed to be under utilizing and eligible to participate in medication interchange and/or cost saving under current prescription benefit coverage can be loaded into the Opportunity Identification & Generation database. For those members, prescription claim histories are targeted by drug listings for use in modeling, wherein suitable alternative medications and current costs are correlated with claim histories for comparison, and cost per fill, cost per year, copay per fill, copay per year, and annual savings are tabulated for easy review and comparison. The more selective analysis can also be useful for batch analysis of a large number of members and their drugs. This may be useful before beginning a marketing campaign, or to target certain member who could achieve large cost savings.

In general analysis is done for all of the drugs a patient in taking including those for a short term that are for acute conditions, however in some embodiments, only long term drugs for chronic conditions are analyzed or presented to the member. This allows the member to focus on the largest opportunities, and simplifies the process for selecting savings opportunities. It also serves to reduce the burden for an approving doctor.

In alternative embodiments, Opportunity Identification & Generation can be used to recommend medication that don't necessarily result in a cost savings, but that is more effective in general or for a particular patient. This improves the quality of care, and may reduce costs in the long term. Similarly, over the counter substitutes may be convenient for a member to purchase, and can reduce visits to a doctor, even though it may be more expensive than a co-payment on a prescription drug.

Opportunity Database 528 can be used to store the result of all the analysis done by OIG 520. The result data may be categorized to provide clinical scores, patient aggregates, household aggregates, plan aggregates, financial scores, savings opportunities, or alternative medications. The database may utilize a series of algorithms to identify a member's combined savings, based on all the prescribed medications where medication alternatives and cost savings are available. It can also be used to provide combined savings opportunities and an efficiency score (e.g. a higher score may indicate greater potential for cost savings). Output from the Opportunity Database 528 is communicated to patients so that they can select one or more cost saving opportunities to take advantage of.

In alternative embodiments, the Opportunity database output may be routed to marketing outreach representatives for direct contact of members to offer the medication substitution opportunities and potential cost savings.

Other components of the My Rx Choices system include the reporting module 524, which is responsible for reporting information back from the physician database 522 and the opportunity database 528 back into the information warehouse. This way information warehouse can have more complete information about doctors and their prescription histories, as well as information about the savings opportunities that were generated.

Marketing component 532 represents the marketing functions of the system such as email campaigns and receiving responses to those campaigns. As described in further detail below, in some embodiments of the invention, possible savings opportunities may be generated for individuals who are not yet members.

Online member experience component 534 provides the interface to the My Rx Choices in an online embodiment. Functions offered though the online component are enrollment, savings opportunity generation, pharmacy benefit plan information and comparison, and spending account balances. Detailed descriptions of the interfaces provided by this component are described below.

Member services 536 is responsible for provide in person service to assist members with services that may not be provided by the online member experience, or that may not be provided for adequately.

Clinical programs 540 receive information from the IW 510, the physicians database 522, and the opportunity database 528. All this information can be combined together to improve clinical programs. Information about drug interactions may be determined as well as the effectiveness of the substitute drugs.

In one embodiment of the invention, the system operates as a client server system with patients using a client computer to communicate with the My Rx Choices 402. Communication can be done through any kind of network capable of connecting clients to the server, for example, the Internet. Client computer can use web based applications or desktop applications to interface with the patient and communicate with the My Rx Choices. Web based clients can be developed using standard technologies like HTML and Javascript, and a web browser. The My Rx Choices itself can be implemented on standard computer systems capable of processing business rules. The system can be developed in a variety of programming languages (i.e. C++, JAVA) and can use various communication technologies (i.e. SQL for database communication). The software itself can be stored on a hard drive, in RAM, or one a removable storage media like CDs or flash drivers. In an alternative embodiment, the system can be designed as a single integrated application designed to be executed on a standalone computer, with all data stored locally, or with use of a network for sending and receiving information.

Figure 6:
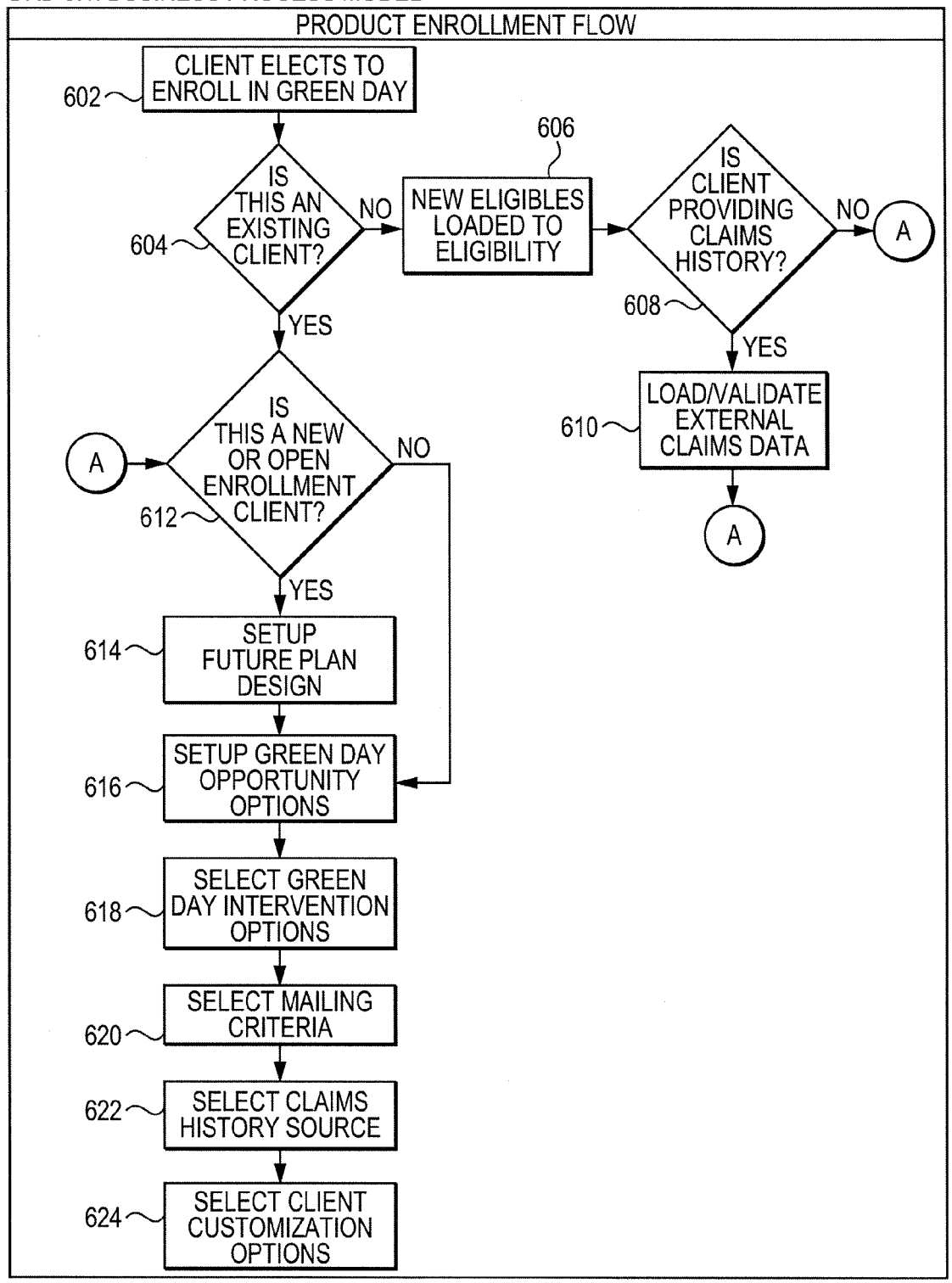
FIG. 6 is a flow diagram showing the enrollment process for a member.

FIG. 6 is a flow diagram showing the enrollment process for a client into the savings program in accordance with at least one embodiment of the invention. Clients 418 (i.e. insurers) need to enroll in the savings program so that the features can be available to the members of their pharmacy benefit program. At step 602, the client elects to enroll in the savings program. At step 604, the My Rx Choices determines if this is an existing member. This may be the case if the company running the My Rx Choices already operates as a pharmacy benefit manager for the insurer. In that situation, the client is only signing up for additional services and the process is simplified. At step 606, if the client is not an existing client, then the newly eligible members are loaded to IW 510 (and eventually eligibility database 514). By loading member data beforehand, when members sign up for the savings program, they only need to confirm the previously entered information, simplifying the signup process. Additionally, this allows the My Rx Choices to confirm they are authorized to use the system. At step 608, it is determined if claims history is being provided, if not the process moves to step 612. Otherwise, claims data is validated and loaded to the IW 510 (and eventually claims database 518). The process then moves to step 612.

At step 612, it is determined if this is an open enrollment client. At step 614, future plan design options are set up. Future plan designs are not yet active for the member, but are needed so that a members can see what their costs will be when next years plan begins. New plan typically begin on January 1. At step 616, the different opportunity options that will be available to the members are determined. These opportunities can include, retail to mail, branded drugs to generic, additional options from the formulary, cross-class brands, cross-class generics, other the counter drugs (OTC), and pill splitting. The opportunities can also vary depending on the member and their plan design. For certain pharmaceutical benefit plans certain substitutions may not generate much cost savings. The opportunities can also vary based on the condition that the patient is being treated for. For more minor conditions, more substitutes may be available, while for more serious conditions less substitutions may be appropriate.

At step 618, intervention options are set for this client. This refers to how the analysis is done and how much information is made available to a member. For example, the savings analysis could be modified not to consider information in the physicians profile database 522, or only to consider it for premium members, or for an additional fee. At step 620, mailing criteria are selected. This determines how members of the client are to be communicated with. Communication methods include a mailed enrollment kit for the member, as part of a broader welcome kit from the insurer, and as a stand alone mailing. Communication can also be done electronically through email or other messaging system.

At step 622, the client selects a claim history source for loading of claim data. At 624, client can select various customization options for their members.

FIG. 7 shows an interface allowing an individual member (i.e. a patient) of the insurer to enroll in the savings program. The following figures describe a client application designed as a web application executable on any web browser. This type of application can be executed on any device, including wireless devices or mobiles phones with a web browser. The enrollment interface collects client profile information for storage in client profile database 516 and/or IW 510. Profile information includes identification information for the patient 702 as well as any other individuals 704 covered by the same pharmacy benefit plan. Enrollment information also includes information on treating doctors 706 to be added to physicians profile database 522. In alternative embodiments, instead of a patient entering enrollment information into the system, they can simply confirm the correctness of information that has already been collected, for example from their enrollment in a pharmacy benefit plan.

FIG. 8 shows additional information that may be included in a plan enrollment process. Patients can request that when purchasing prescriptions through the My Rx Choices, that lower costs options 802 are always dispensed for them. This simplifies the process for saving money, since the default option will be to dispense a cheaper generic medication. Further, to insure that more expensive brand name medications are not dispensed, a warning 806 can be sent to the patient. Similar to the above options, the 90 day option 804 increases convenience by mailing large amounts of medications to a patient at once.

FIG. 9 shows an interface allowing a patient to have an analysis done on the medications they are currently taking. The interface allows a patient to easily confirm the proper person is being analyzed using drop down box 902. This also makes it easy for other household members, such as children, to be analyzed. For the selected patient, area 904 shows the currently prescribed medications. This information can be populated from IW 510, which contains prescription claims information for the patient. The patient can select one or more medications to be analyzed for substitutes, and then continue to the next step of the process using button 908. If a specific medication cannot be found, for example because it is a new prescription, it can be searched for using a search feature accessed through link 908.

Figure 10:
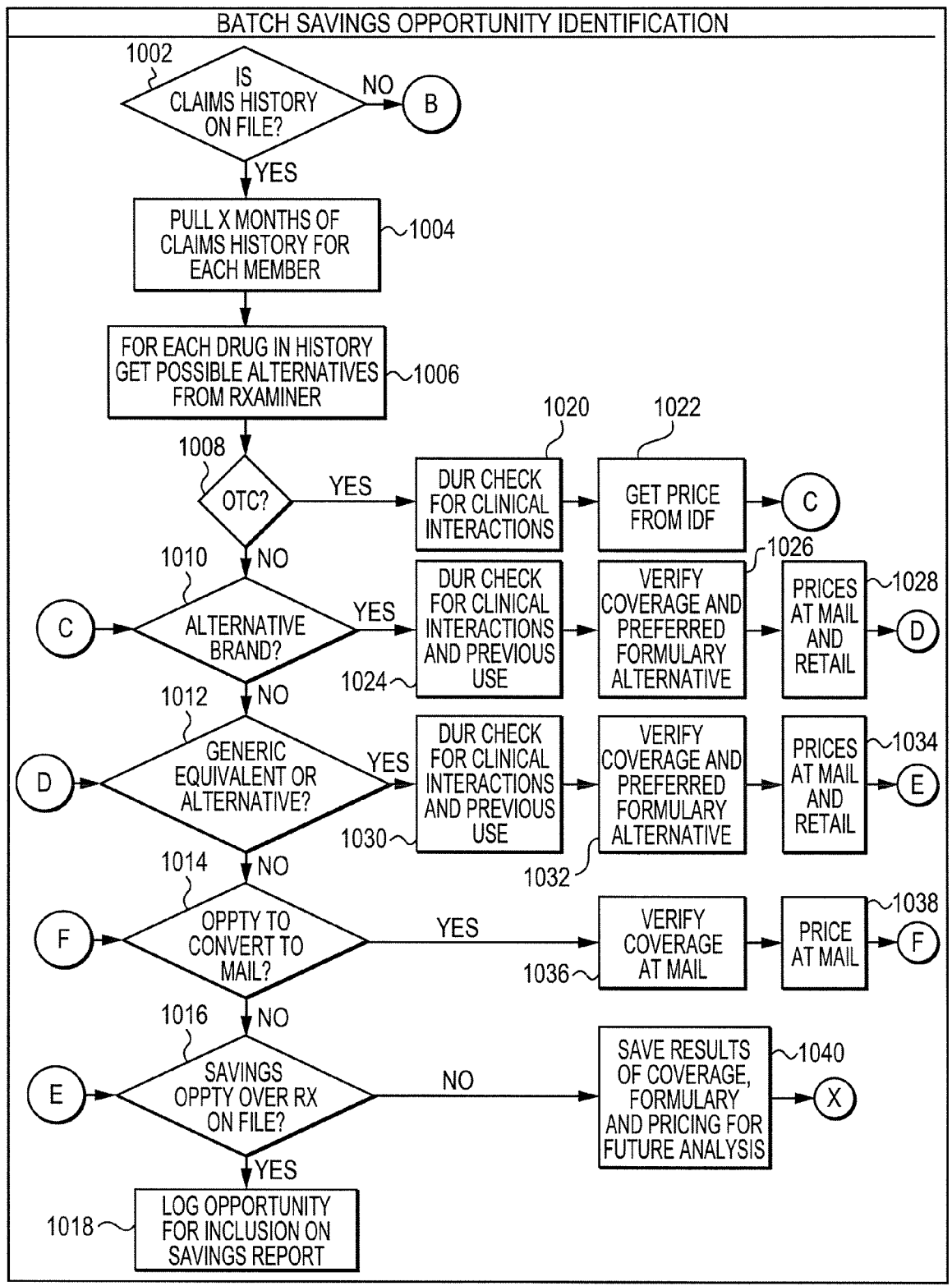
FIG. 10 is a flow diagram showing how a member's prescriptions are analyzed.

FIG. 10 is a flow diagram showing how a patient's prescriptions are analyzed. The process starts at step 1002 by determining if any claim history information for the member is available in the IW 510. If not, although substitute medications can be determined, possible savings cannot be calculated.

At step 1004, claim history for the member is retrieved from IW 510. At step 1006, each of the medication is analyzed for alternatives. Older prescriptions are also retrieved giving a chance for the member to selectively drop medications they are no longer taking. Additionally, members can also search for a new drug they are either researching, took in the past, or which their doctor has prescribed but they haven't started taking yet. Alternatives for medications are determined using medication database 530 and opportunity identification and generation component 520 as described with respect to FIG. 5. At step 1008, it is determined if there are any OTC replacement medications for the member, if so, at step 1020 they are analyzed for possible medication interactions. Such analysis can be done using medication information, and information from a member's health assessment questionnaire 502 they filled out. At step 1022, the prices are retrieved from a database. If not OTC substitutes are found the process moves directly to step 1010.

Next the member's medications are checked against alternative brands at 1012. These are also branded medications, but medications that may be less expensive and have a similar therapeutic effect. At step 1024, these medications are checked for interactions similar to step 1020. At step 1026, the member's pharmacy benefit plan from health manager database 525 is checked for coverage for this alternative branded medication, and to see if it is a preferred formulary alternative. At step 1028, the alternative branded medication is priced at mail and retail prices to determine savings for the member. The process then moves to step 1012. If no branded alternatives are found, the process moves directly to step 1012.

At step 1012, the member's medications are checked against alternative and/or generic drugs. If there is a substitute, the medication is checked for interactions, coverage is verified, and it is priced similar to steps 1024, 1026, and 1028. The process then moves to step 1014. If no generic and/or alternative drugs are found the process moves directly to step 1014.

In an alternative embodiment, when performing an analysis to determine the substitute medications that can be recommended for a patient, drug interactions for the individual and their prescriptions are considered. The drug interaction review can include not only those drugs a patient is currently taken or has taken in the past, but can also incorporate information from other sources, such as laboratory test results. Use of laboratory test results allows a better determination of the patient's health and medical condition. Although a recommended substitute drug may not normally cause any adverse interaction, later lab result may in fact show an undesirable interaction. This data from lab results can be stored in POLAR 504 for retrieval during analysis of substitute medications. Additionally, laboratory results can be used to confirm or deny the effectiveness of the substitute medication for the patient. This can be incorporated when the patient attempts to reorder a medication, or when other substitute medications are recommended for a patient. Further details of a system that can be utilized advantageously with the present invention and which describes the use of laboratory data can be found in U.S. Pat. No. 7,124,031 issued to Medco Health Solutions Inc., which is hereby incorporated by reference in its entirety.

At step 1014, it is determined if the medication is one that can be converted to a mail opportunity, if so at step 1036 coverage is verified. At step 1038, the medication is priced at mail and the process moves to step 1016. At step 1016, it is determined if there are savings over the prescriptions currently on file for the member. If there are saving opportunities (or other advantageous substitutions), then at step 1018, those opportunities are saved to be included in a savings report to the member. If there is a not a saving opportunity then at step 1040 the results of the coverage, formulary, and pricing is saved for future analysis. This data can be used to understand client opportunities and change the design of a pharmaceutical benefit plan.

Figure 11:
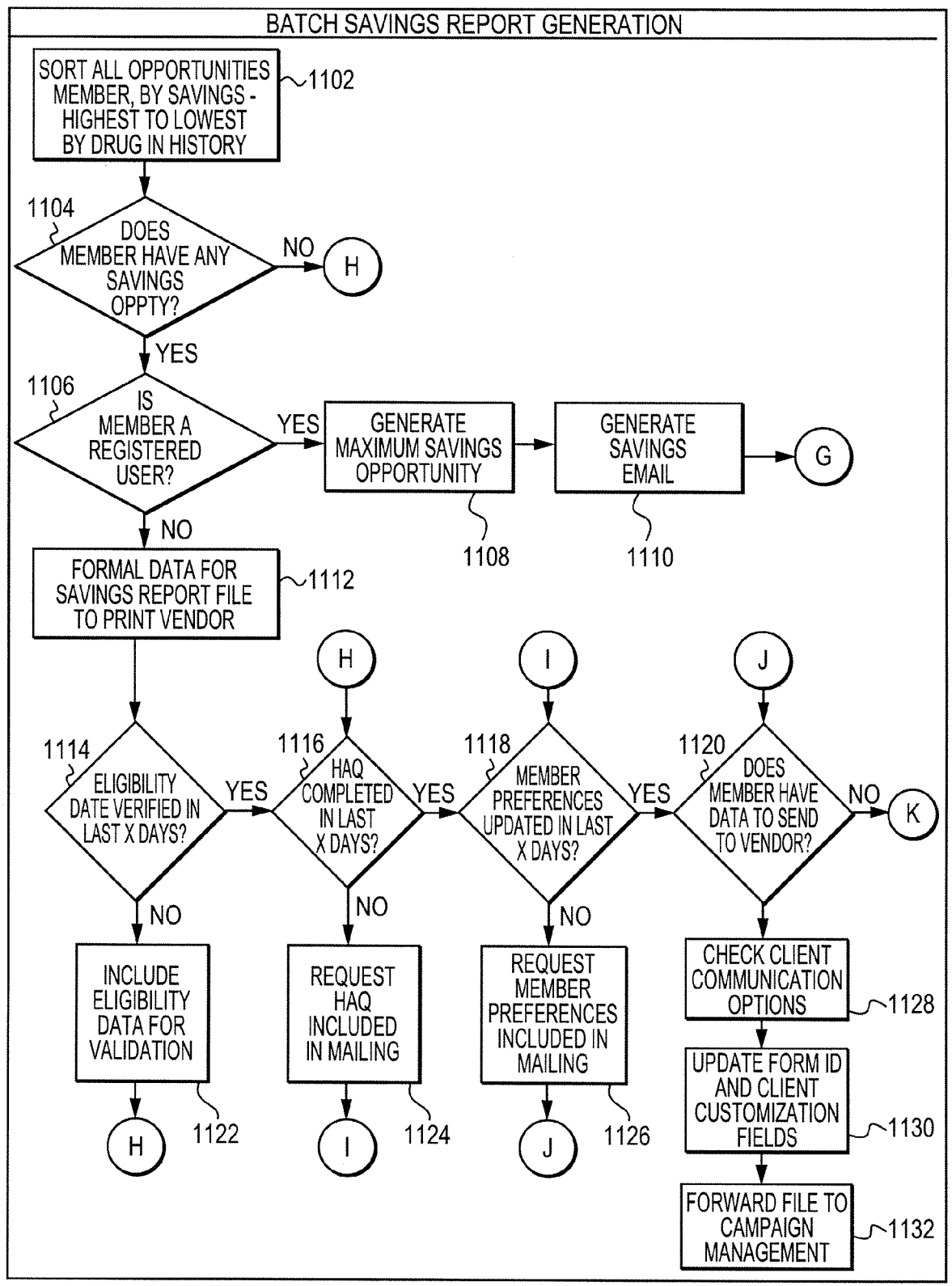
FIG. 11 is a flow diagram showing how a report is generated based on the analysis.

FIG. 11 is a flow diagram showing how a report is generated based on the analysis described with respect to FIGS. 5 and 10. This process is related to a user who is a member and will immediately be receiving savings information, such as through a web interface or email. It is also related to an alternative embodiment of the system as applied to individuals who are not members of a client to the pharmacy benefit manager program. These individuals may still received savings reports through the PBM. This can be for marketing purposes to encourage them to join a particular client of the PBM, or simply to inform them of the savings possible through switching to alternative medications.

At step 1102, all the previously determined opportunities from FIG. 10 are organized for the member. They can be sorted by savings amount from highest to lowest and grouped by medication for easy selection by the member. At step 1104, if there are no savings opportunities when the sorting was attempted, if so the process ends. Otherwise at step 1106, it is determined if the member is a registered member. If the member is a registered member, then the maximum savings opportunity is generated and an email is sent to the member. Alternatively, the saving opportunities may be displayed in the client interface, such as a web browser. Further details are described with respect to FIG. 12.

If it is determined that determined at step 1106 that the member is not a registered user then the results are formatted and saved to be printed for distribution to the member. At step 1114, if eligibility data has been verified within a specified period of time then the process moves to step 1116, otherwise eat step 1122 eligibility data is include for validation in any communication with member. At step 116, if a HAQ has been completed within a specific period of time, the process moves to step 1118, otherwise at step 1124 a HAQ is requested in any communication with member. At step 1118, if member preferences have been updated within a specified period of time, the process moves to step 1120, otherwise at step 1126 a request for member preferences are included in any communication with the member. At step 1120, if a member has data to send to a vendor then the process moves to step 1128, if not the process ends. At step 1128, the client communication preferences are checked, updated at step 1130 with information from the client customization fields, and forwarded to campaign management at step 1132. Campaign management can be any process or person involved in distribution these saving opportunities to the member.

FIG. 12 shows an interface allowing a patient to select a substitute medication. This is one interface that can be used to display the different savings opportunities available to a member after an analysis have been done on their medication claim history as described in FIGS. 5 and 10. This interface can be presented in response to the member's selection of medications as shown in FIG. 9. This interface may be changed in any number of ways, including displaying only a single medication at a time, or providing additional information about the substitute medication (side effects etc.). This interface can also include multiple prices for the substitute medication based on the source they are purchased from. A member may have 3 different local pharmacies which different prices for the medication. Mail order pharmacies might have yet other prices. The lowest of these prices can be displayed for the member, or the member can be allowed to select between them. This can allow a member to choose a more convenient location, one with better service, or one that can provide the medication sooner.

The medications that a patient is currently taking 1202, the corresponding cost 1206, and the corresponding delivery method is shown in the left column of the interface. A substitute medication 1208 that would result in a cost savings for the patient in shown in the middle column. Next to the substitute medication is the corresponding cost of the medication 1210 per year and per month, and the corresponding delivery method. The third column shows the patient the amount that would be saved by purchasing the substitute medication instead of the drug the patient is currently taking. There is also a link 1216 to other alternative drugs that are substitutable for the drug the patient is currently taking, but are not the first recommendation. This can be because the drug does not result in as great a savings (or none at all), or is not as effective, but it can also be because the drug may have side effects, or the chance of complications with other drugs the patient is taking. The interface also shows a total cost savings 1218 if the patient were to choose all the lower cost substitute drugs offered.

Using selection buttons 1224 and 1226 the patient can choose to remain with their current drug, or switch to the offered lower cost substitute drug. After making their selections a patient confirm the selections and request approval in the following screen using continue button 1220. If the patient would like to have different drugs analyzed they can go back to the drug selection interface using button 1222.

FIG. 13 shows an alternative interface allowing a patient to select a substitute drug. In this interface the patient is given different substitute drugs based on the source of the recommendation. This example shows a pharmacist's recommendation 1302 and the corresponding savings 1312, an over the counter recommendation 1304 and corresponding saving 1314, as well as other branded substitutes 1308 and 1310 (these may not result in savings, but may be more effective or have less side effects). The patient's current drug 1306 and corresponding cost 1316 is also shown for comparison purposes. The patient can select the desired drug and delivery method using selection buttons next to the drug, for example buttons 1320 and 1322. The maximum total saving that can be earned by patient 1318 is shown in the upper right of the interface. Alternatively, this number can be dynamically updated to correspond to a user's current selection (e.g. using javascript).

FIG. 14 shows an interface informing the patient about getting a doctor's approval for the substitution of a drug in accordance with at least one embodiment of the invention. For some drugs the doctor can automatically be contacted for approval by the pharmacy benefit manager, for other drugs, the patient has to contact the doctor themselves.

The interface shows a patient's current prescription 1402 along with their newly selected drug 1404. Column 1406 shows who will be contacting the patient's doctor about the change in prescription. The selection buttons 1408 and 1410 allow the patient to select the pharmacy benefit manager or themselves, respectively. Contact information for the doctor 1412 is also shown on the interface.

The interface also shows drugs for which only the patient can directly contact the doctors. This can be the situation for choosing a drug that the patient is not currently taking, or for selecting a controlled substance. The drugs 1414 and 1416, are shown along with the corresponding substitute drugs 1424 and 1426. There is only one selection option 1418 for these drugs.

In an alternative embodiment, all the medications selected for substitution by the member are sent to a prescribing doctor or authorizing health care professional for approval. Although they may require more consideration by the doctor, and/or may be more likely to require a visit of consultation, requests for approval can still be automatically sent. The doctor can always contact the patient for additional information if they desire.

After making the appropriate selections, the patient can either confirm using button 1422, or go back to the previous interface to change their selections (FIG. 12 or 13) using button 1420.

FIG. 15 shows an example interface allowing a patient to confirm their request for approval to a doctor. The interface shows 1502 the drugs that the patient must contact the doctor themselves for approval. A convenient link 1504 is provided so that the patient can easily print out the necessary information for discussion with their doctor before making a change. Shown below these drugs at 1506 are those drugs for which the PBM can directly contact the doctor. To complete this request, a user clicks on link 1508. To encourage the patient to get approval, the potential savings benefits are again shown at 1510 and 1512.

FIG. 16 shows an interface used by a doctor to approve substitutions that have been submitted by the pharmacy benefit manager. The interface lists the patients and provides a simple way for the doctor to respond to each of the requests. This information is transmitted back to the My Rx Choices 402 for processing.

The interface lists the doctor's information 1602 at the top, along with a link to the formulary 1604. This allows the doctor to better understand the drug substitutions. The date of the request 1606 is also shown at the top. Requests may be sent instantly, daily, or weekly to a doctor depending on the doctor's and PBM's preferences. Column 1602 lists the patients name and/or other identification information; Column 1610 lists the patient's gender; Column 1614 lists the patient's current prescription; and Column 1616 lists the patient's request. Further details about the request are available using the provided link 1626.

To take an action with respect to a request, the doctor uses the selection boxes in column 1618. Options available to the doctor include, approved 1620, denied, and must see patient 1622. After the doctor has completed his selection he can submit them to the My Rx Choices using link 1624. In an alternative embodiment, the interface can show information about only a single patient at a time. In yet other embodiments, options can be provided to allow an action to be taken with respect to multiple, or all, patients at once. Additionally, requests to the doctor can be organized and sorted in different ways. Although this request is shown organized by date, requests to the doctor can also be organized by drug. For example, all patients on a particular drug can be approved for an alternative drug at the same time. Requests can also be organized by health condition, to make it easier to the doctor to understand the condition of the patients.

Figure 17:
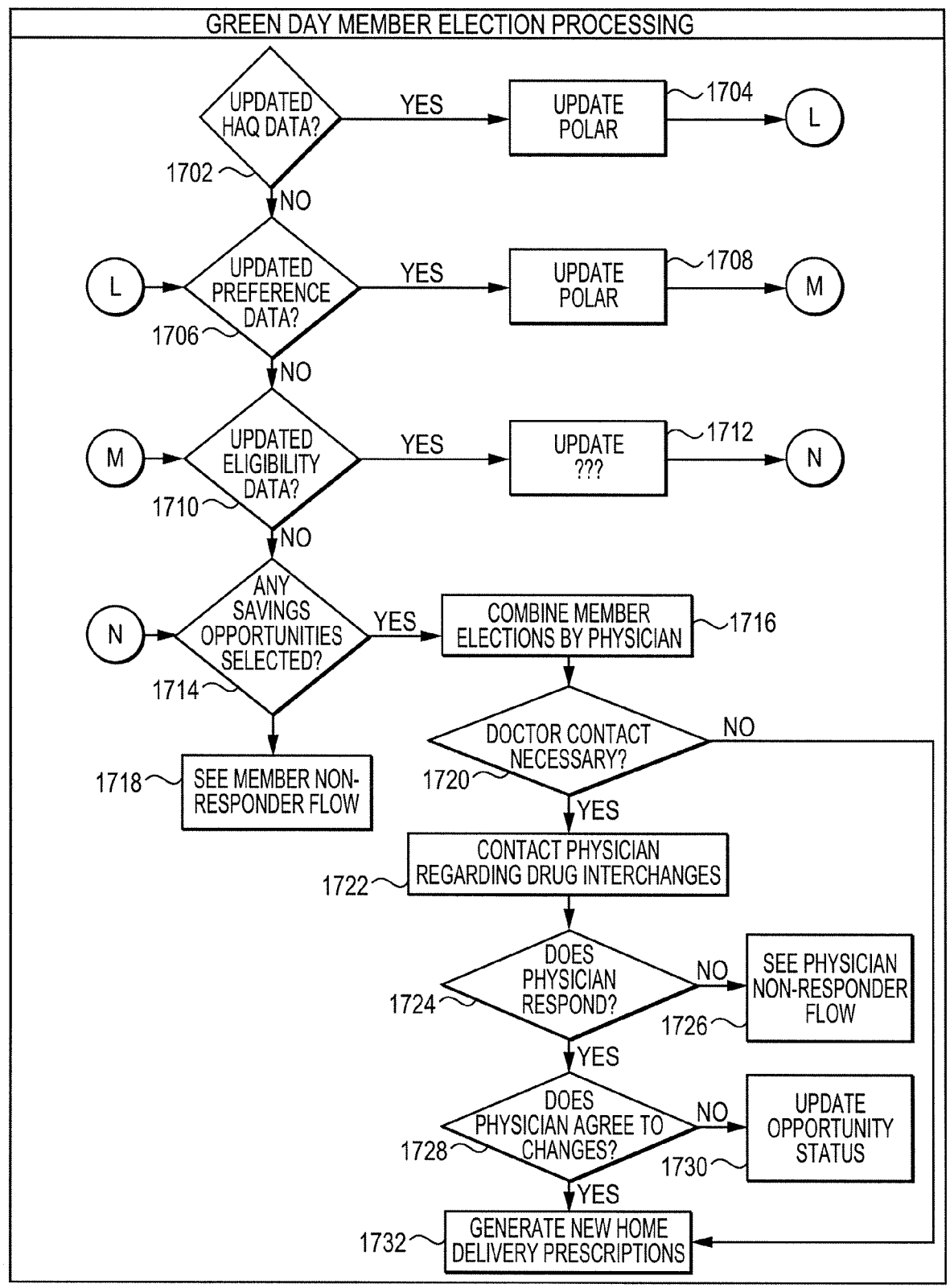
FIG. 17 is a flow diagram of the member's election process and approval by a doctor.

FIG. 17 is a flow diagram of a doctor responding to a drug substitution request along with updated member processing. Before the requests are sent to the doctor, member information is updated to ensure accuracy.

At step 1702, member information in IW 510 is checked for an updated HAQ. This is important as it may contain new allergy information or other data. If there is an update, then at step 1704 HAQ 502 it is integrated into POLAR 504. At step 1706, member information is checked for updated preferences, and if necessary POLAR is appropriately updated at 1708. At step 1710, member information is checked for updated eligibility data, and updated if necessary at 1712.

At step 1714, the patient's selected saving opportunities are reviewed, if none are found at 1718, the process ends. At step 1716, the selected opportunities are gathered by doctor and organized so that the doctor can respond to the selections. At step 1720, it is determined if doctor contact is necessary. In some embodiments with a PBM's or doctor's prior approval, no specific approval may be necessary from a doctor to switch to a generic equivalent of a branded drug. In these type of situations when no contact is necessary, new prescriptions are generated at step 1732, and the process ends.

If contact is necessary, at 1722 a request as described with respect to FIG. 16 is sent to the doctor. At step 1724, it is determined if a response has been received from the doctor. If not, a reminder can be sent or other steps can be taken to get approval at step 1726. At step 1728, if the doctor has agreed to the changes, then new prescriptions are generated at step 1732. Otherwise, at step 1730 the status of the opportunity is updated, which may mean canceling it and presenting different opportunities for the patient to choose from. The doctor's selection can be saved not only for a particular patient, but can be saved in physician profiling database 522 for later analysis and use during the opportunity generation process.

Figure 18:
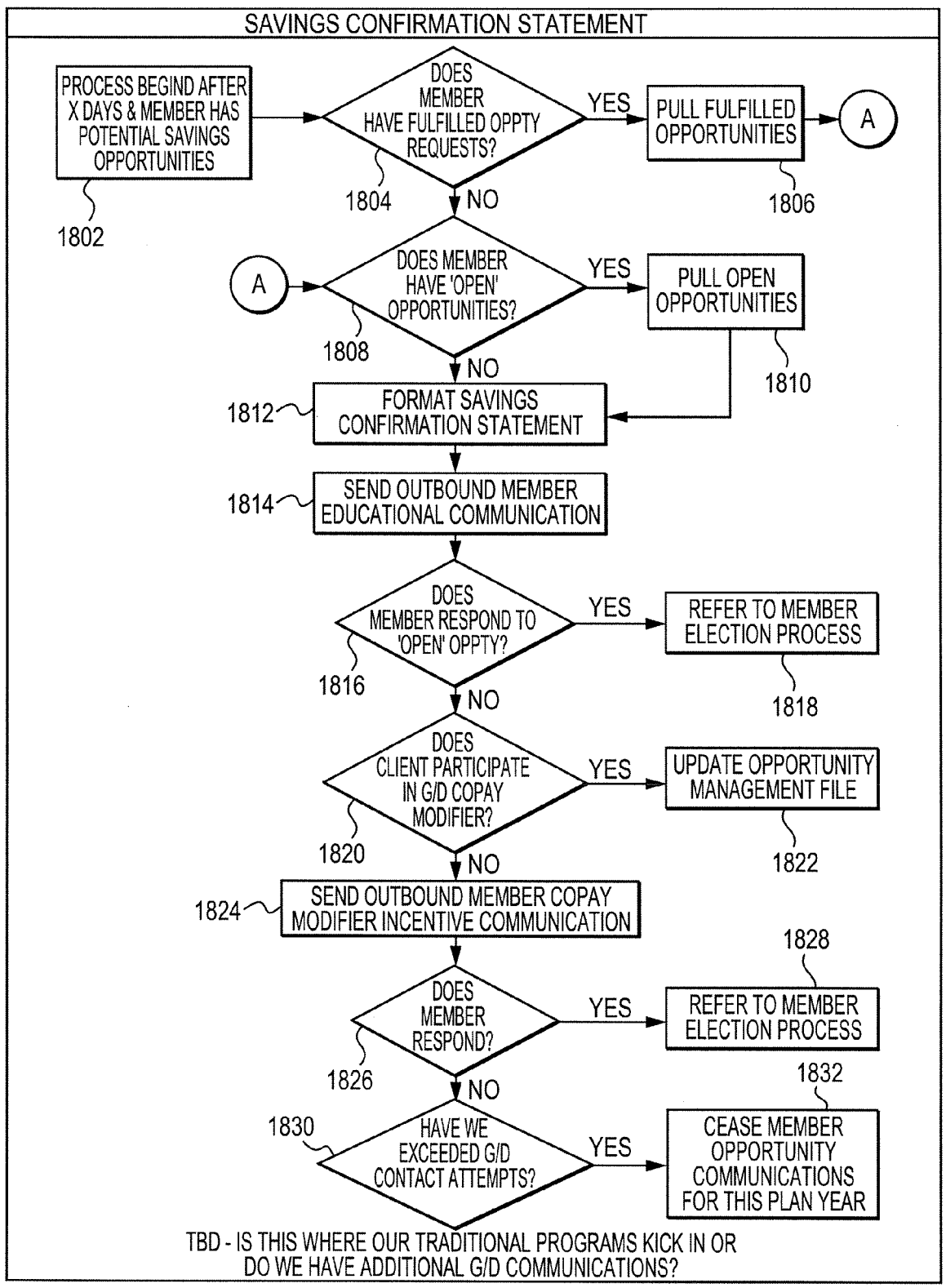
FIG. 18 is a flow diagram confirming a patient's savings.

FIG. 18 is a flow diagram confirming and reporting a patient's substitutions. This is an important part of the process that can reinforce the benefits and savings of the substitutions to the member. The process begins at step 1802 after savings opportunities have been sent out for approval. At step 1804, information related to the patient is checked for fulfilled requests. At step 1806, the corresponding approvals are retrieved from the IW 510 or other database storing the doctor's responses. At step 1808 open savings opportunities are also pulled. Once all the opportunities have been pulled, at step 1812 the approved ones can be formatted into a savings confirmation statement for the member. At step 1814, this communication is sent to the member. This communication can include a reminder of the additional savings opportunities. In a web interface, this communication can be another interface screen or popup box.

At step 1816, if the member has responded to the open opportunity savings then they are referred to the selection process. Otherwise, at step 1820, if a member participates in the co-pay modifier program, to encourage their response and selection of cost saving opportunities, various co-pay incentives can be offered. This can includes reduced or eliminated co-payments. At step 1824, these incentives can be communicated to the client. If the member responds, at step 1826 they are again referred to the savings opportunity selection process, similar to step 1818. Otherwise, if there is no response, then at step 1830 if the number of contact attempts has not been exceeded, follow up communications are sent. After all the attempts have been completed for the year, the process ends as shown at step 1832.

Figure 19:
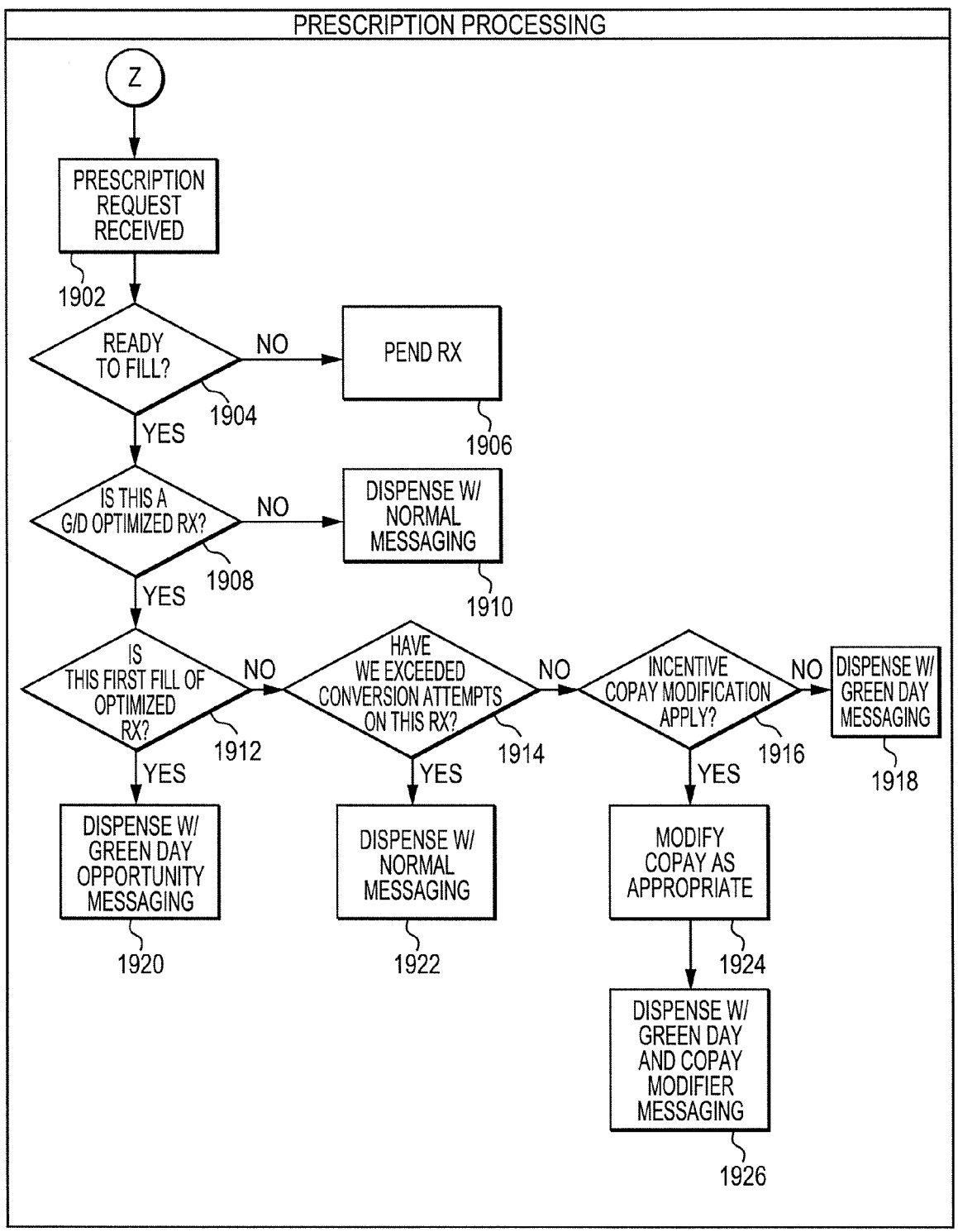
FIG. 19 is a flow diagram showing how prescriptions are processed.

FIG. 19 is a flow diagram showing how prescriptions are processed. The process begins at step 1902 where prescription requests are received. If the prescription is ready to be filled at step 1904, then a check is made at step 1908 to see if this prescription is being filled in response to a savings opportunity and a doctor's approval. If the prescription is not ready to be filled, then it is pended at step 1906. If the prescriptions are not being filled in response to a savings opportunity, the normal messaging is sent along with the prescription. However, for those prescriptions that do correspond to those from savings opportunities, special messaging can be used, reinforcing again the savings and benefits (e.g. more effective medication) the customer has received. At step 1912, if this is the first filling of an optimized prescription a special message is applied at step 1920. Otherwise, the prescription is checked to see if it was part of an incentive co-pay modification purchase at step 1916. If so, then at step 1924 the co-pay is modified and at step 1926 the prescription is dispensed with special messaging. At step 1928 those prescriptions that are saving opportunities, but are not being filled for the first time, and are not special incentive purchases, are filled along with messaging about the savings.

Figure 20:
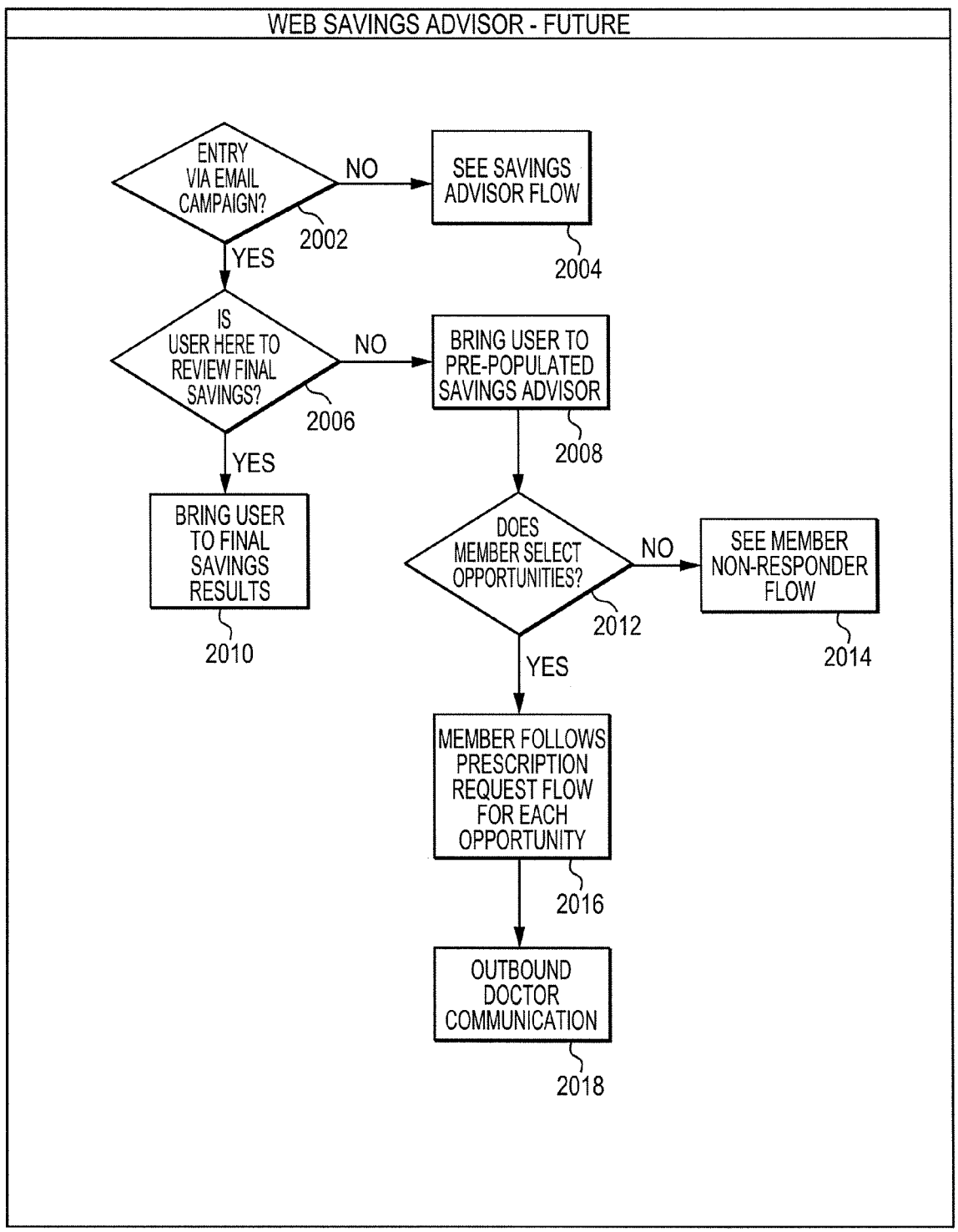
FIG. 20 is a flow diagram showing use of the invention through email.

FIG. 20 is a flow diagram showing how the My Rx Choices can be incorporated into an email marketing campaign. Although embodiments of the invention above have been described in the context of a system that allows members with a particular insurer and pharmacy benefit plan to save money by switching to lower cost drugs, the system can also be applied to any individual. Even though detailed information about their pharmacy benefit plan may not be available, possible savings opportunities can still be generated based on known substitute drugs and more general information about pharmacy benefit plans. This type of "universal" embodiment can be used in a marketing campaign to attract patients to a particular pharmacy benefit plan or to have them sign up with the system implemented by the savings manger 402. It can also be used by generic and other substitute drug manufactures to encourage patients to switch to their products.

In this type of "universal" embodiment, a website can be set up where users can sign up an enter information about the drugs they are currently taking. Based on this appropriate substitutes can be suggested. Without particular pharmacy benefit plan information, it cannot be known whether those alternative would be covered, and the amount of saving that would be generated, however it alerts the patients to fact that alternatives exist. This may encourage the patient to discuss it with their doctor. To bring people to the website, email may be sent out.

At step 2002, it is checked if an individual has entered a website from an email campaign. If not, this is a regular member and they can use the system normally. At step 2006, the individual may desire to review final savings available, these savings are final compared to any estimated or suggested savings based only on the drugs the patient was currently taking. At step 2010 the final savings information is shown based on more detailed information about the individuals pharmacy benefit plan. This information is stored in the system and can be retrieved for the member. In an alternative embodiment if this information is not available or incomplete, a member can enter in information that will help determine a final savings amount. At step 2008, the user is show a pre-populated My Rx Choices based on any known information about what drugs they are taking. At step 2012, if the patient indicates they would like to explore a savings opportunity further, then at 2016 they are led through a series of interfaces that collect additional information. A final savings amount can be determined, and their doctor can be communicated with. At 2018 the doctor is sent a communication for approval. At step 2014, because no opportunities were selected the process end.

This above method allows an individual who may no be a member of a participating insurance program to still get the benefits of the My Rx Choices, by entering additional information themselves that would normally be in the health management database 525 and IW 510.

Figure 21:
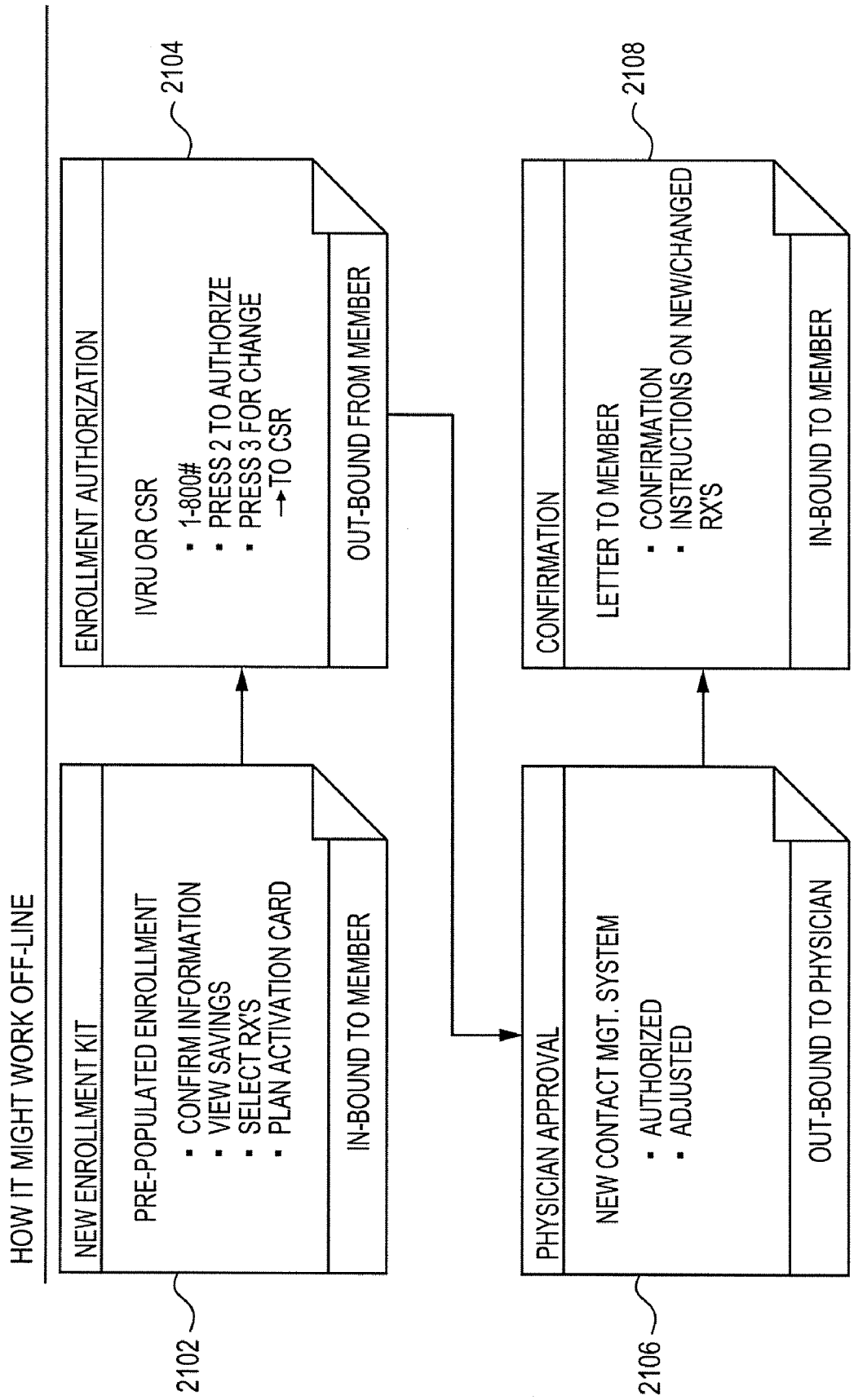
FIG. 21 shows an off-line embodiment of the invention.

FIG. 21 shows an off-line alternative embodiment of the invention that can be used alone, or in combination with other embodiments of the invention. In this embodiment, instead of using a web, or other electronic interface, the savings opportunity selection process and ordering steps are done through the mail or phone. At step 2102, a new enrollment kit with information is mailed out to a member. The kit can contain confirmation information, information on possible savings, selected prescriptions, and a plan activation card. In response to this, the member can enroll through the mail or phone. Step 2104 shows phone authorization using an 800 number, and an automated response system. The phone interface can be used to authorize enrollment and offer savings opportunities for the member to select from. After the selections have been made, at step 2106 the My Rx Choices 402 can contact the doctor for approval. After responses have been received, a confirmation can be sent to the member at step 2108 along with any instructions for the new medications.

Figure 22:
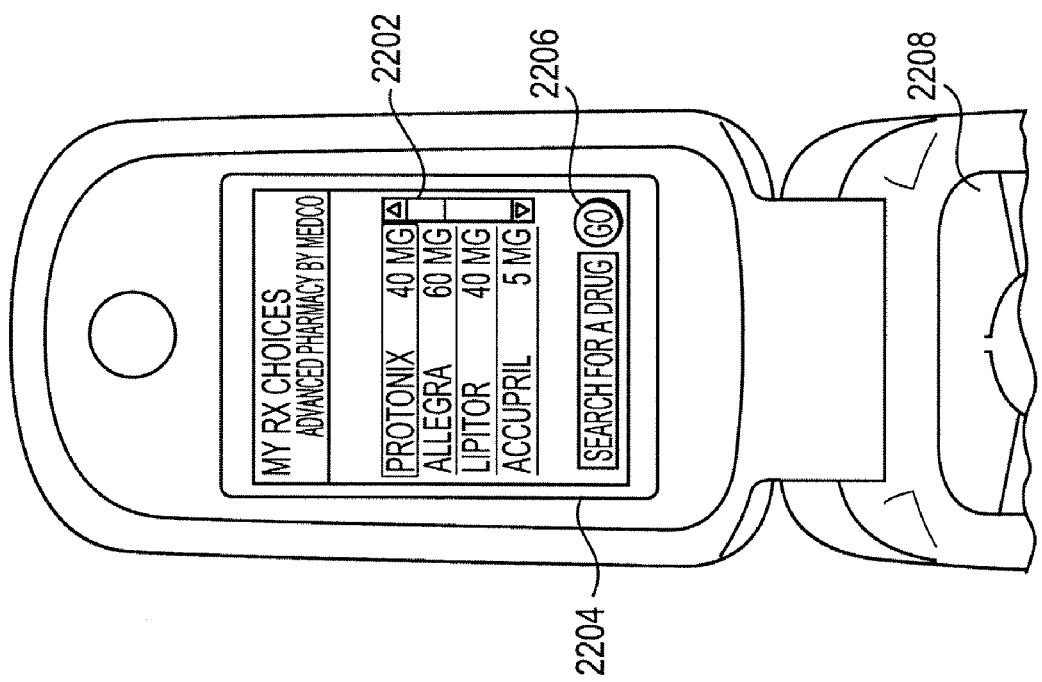
FIG. 22 shows a mobile phone embodiment of the invention and substitution of a medication.

FIG. 22 shows an alternative mobile phone embodiment of the invention that can be used alone, or in combination with other embodiments of the invention. This embodiment is based on a mobile web application, or native application on the phone. A very similar interface could be implemented with a short messaging system (SMS), although it would be text based and less interactive. Many people today have a mobile phone, and keep it on their person, in contrast to always having a computer capable of executing web based applications. Therefore a mobile phone based embodiment of the invention is extremely convenient, and can offer a away to immediately check whether a prescribed medication is cost effective or not for the member. The member can even do this in the doctor's office, before or after, the doctor writes the prescription. Alternatively, or in addition, wireless mobile computing devices such as devices provided by Research-In-Motion's Blackberry devices, pocket PCs, and the like may also be used that employ more typical wireless IP based protocols.

In detail, after logging in, a member is shown a list of drugs 2202 that they are currently taking and want to analyze for substitutes. Alternatively, a member can search for a drug using input field 2204. To submit their choice for analysis, button 2206 can be used. Interaction with the interface itself can be done using the standard buttons built into the phone such as button 2208.

Figure 23:
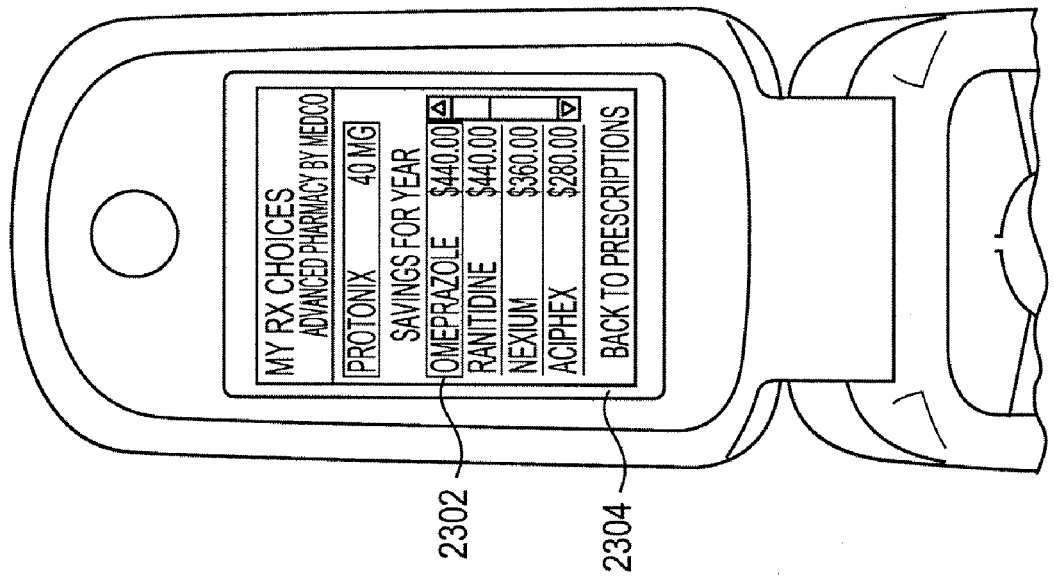
FIG. 23 shows a mobile phone embodiment of the invention and the available choices.

FIG. 23 shows a mobile phone embodiment of the invention and the available choices. The user can select one of the listed choices 2302, or they can go back using link 2304 and select a different drug.

Figure 24:
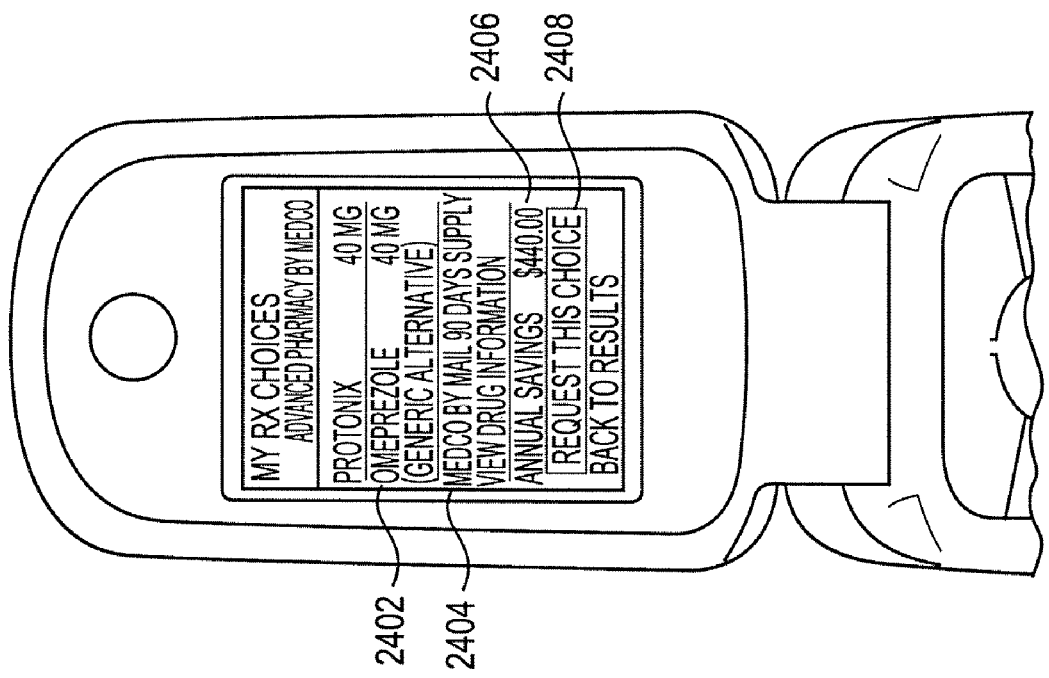
FIG. 24 shows a mobile phone embodiment of the invention and selection of one of the alternatives.

FIG. 24 shows a mobile phone embodiment of the invention and details about the selected alternative drug. The drug name 2402 is listed along with the type of substitute it is. Additional information can be obtained by using link 2404. The potential savings 2406 are also displayed for the member. Finally, link 2408 allows a member to confirm their selection.

Figure 25:
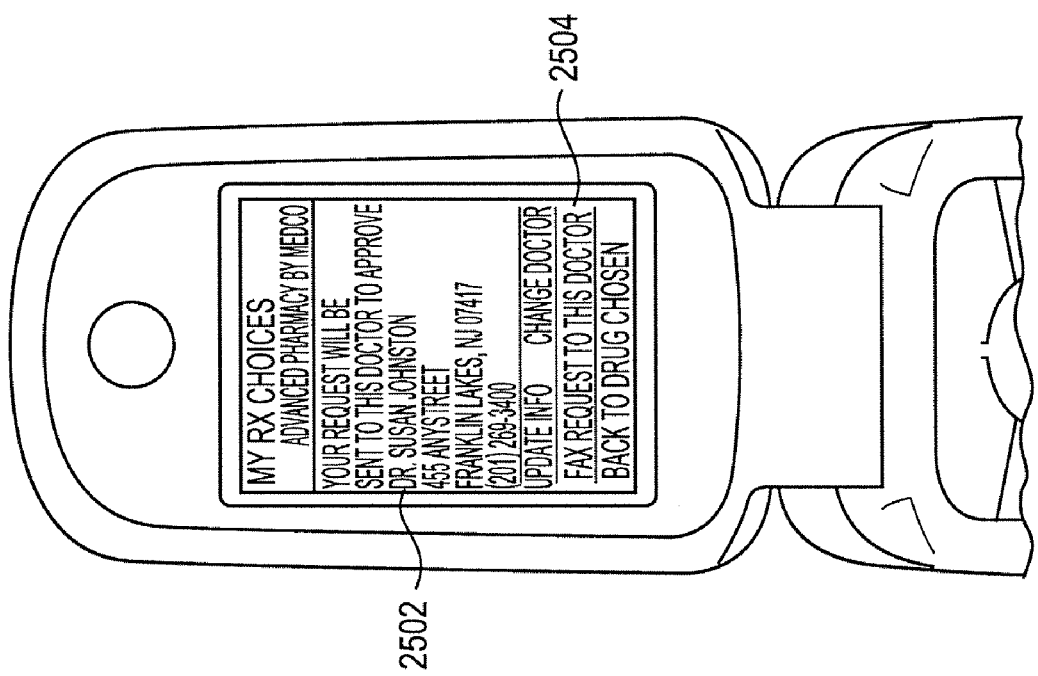
FIG. 25 shows a mobile phone embodiment of the invention and sending the choice to a doctor for approval.

FIG. 25 shows a mobile phone embodiment of the invention and sending the choice to a doctor for approval. The doctor's contact information is displayed 2502, and a link 2504 is provided to send this request to the doctor. This embodiment shows sending a fax to the doctor. In other embodiments, the request can be handled in the same way as the web interface and bundled along with other requests to the doctor as shown in FIG. 16.

Figure 26:
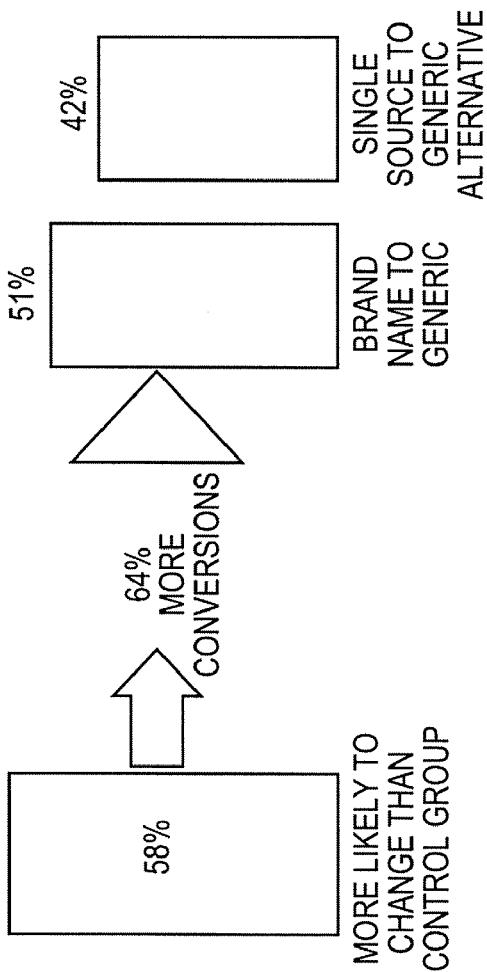
FIG. 26 is a summary chart of the savings achieved by members who used the My Rx Choices.

FIG. 26 shows the significant savings achieved by members using an embodiment of the invention implemented as a web based application. As shown in this summary diagram, 27,850 members were followed as they used the My Rx Choices in April 2006. Those members switching to a lower cost drug were tracked. The results show that members using the My Rx Choices were 58% more likely to change to a lower cost drug than a well-matched control group of member who did not use the My Rx Choices. There were also 64% more conversions to lower cost alternatives. Further, 51% of people switched from a brand name drug to a generic drug, while 42% switched from a single source drug to a generic alternative. By using the My Rx Choices the average member saved $171 per years for each drug switched.

Figure 27A:
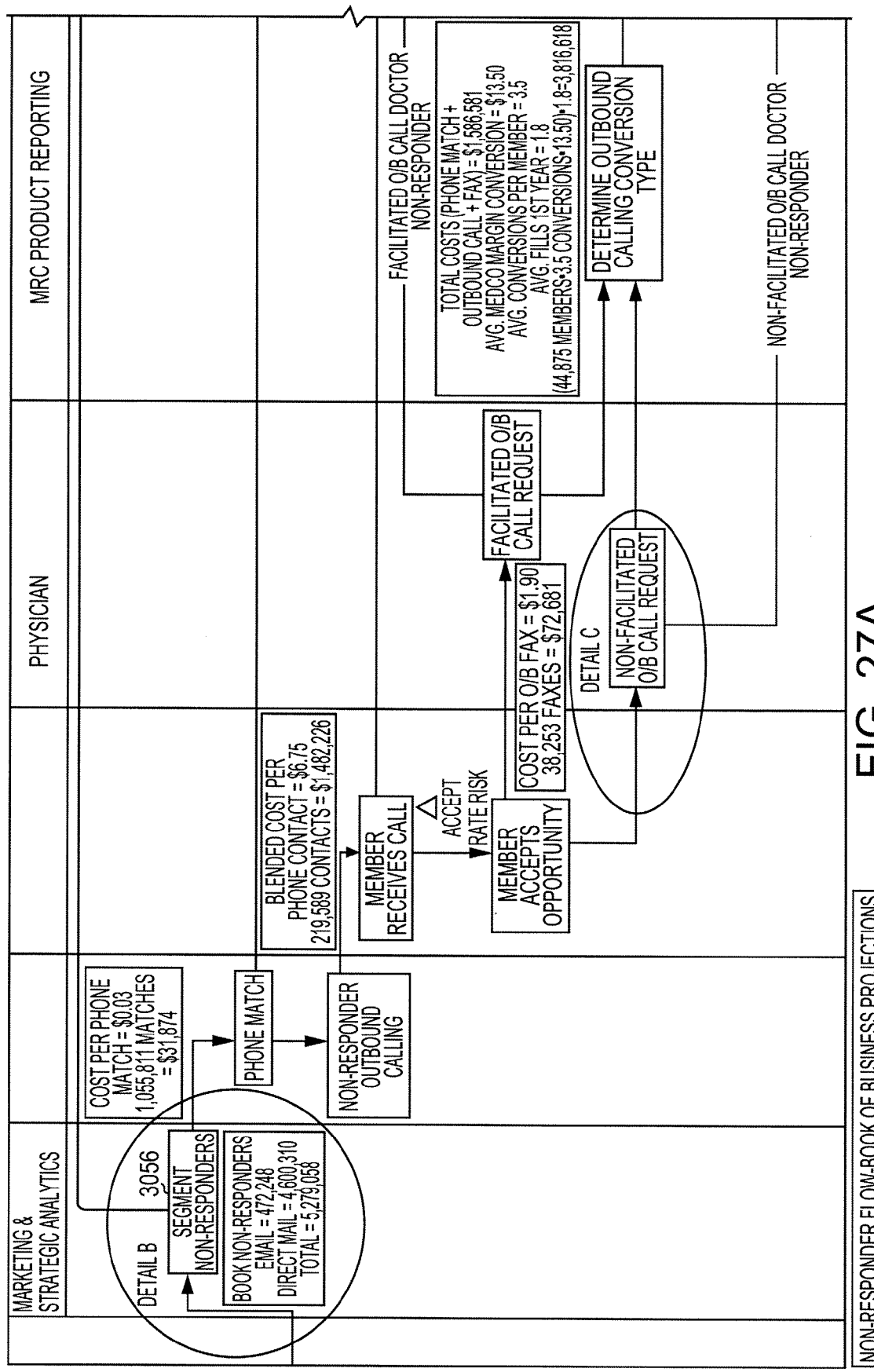
FIG. 27 is a detailed diagram of the savings achieved by members who did not use the My Rx Choices.
Figure 28A:
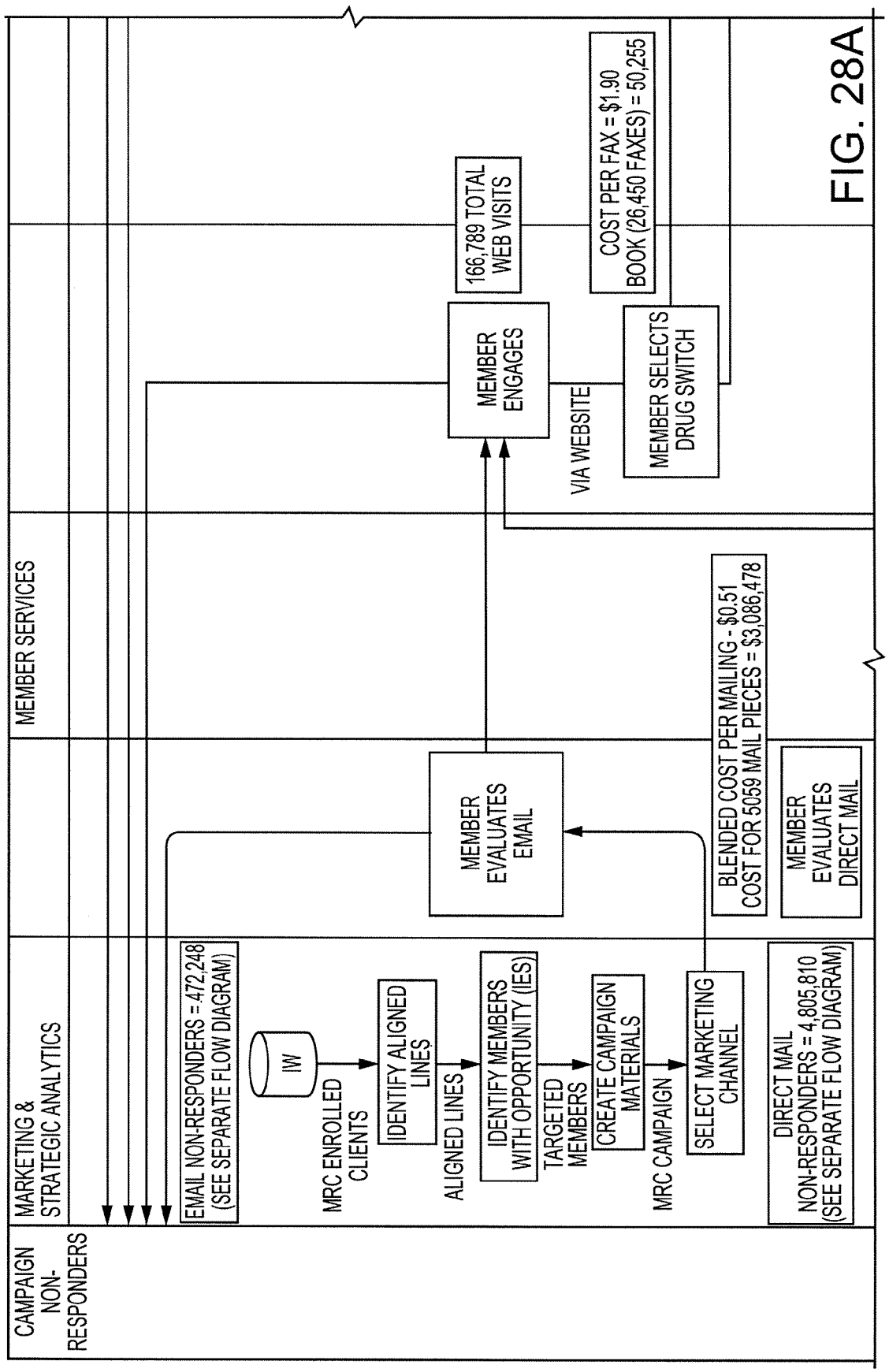
FIG. 28 is a detailed diagram of the savings achieved by members who used the My Rx Choices.
Figure 28C:
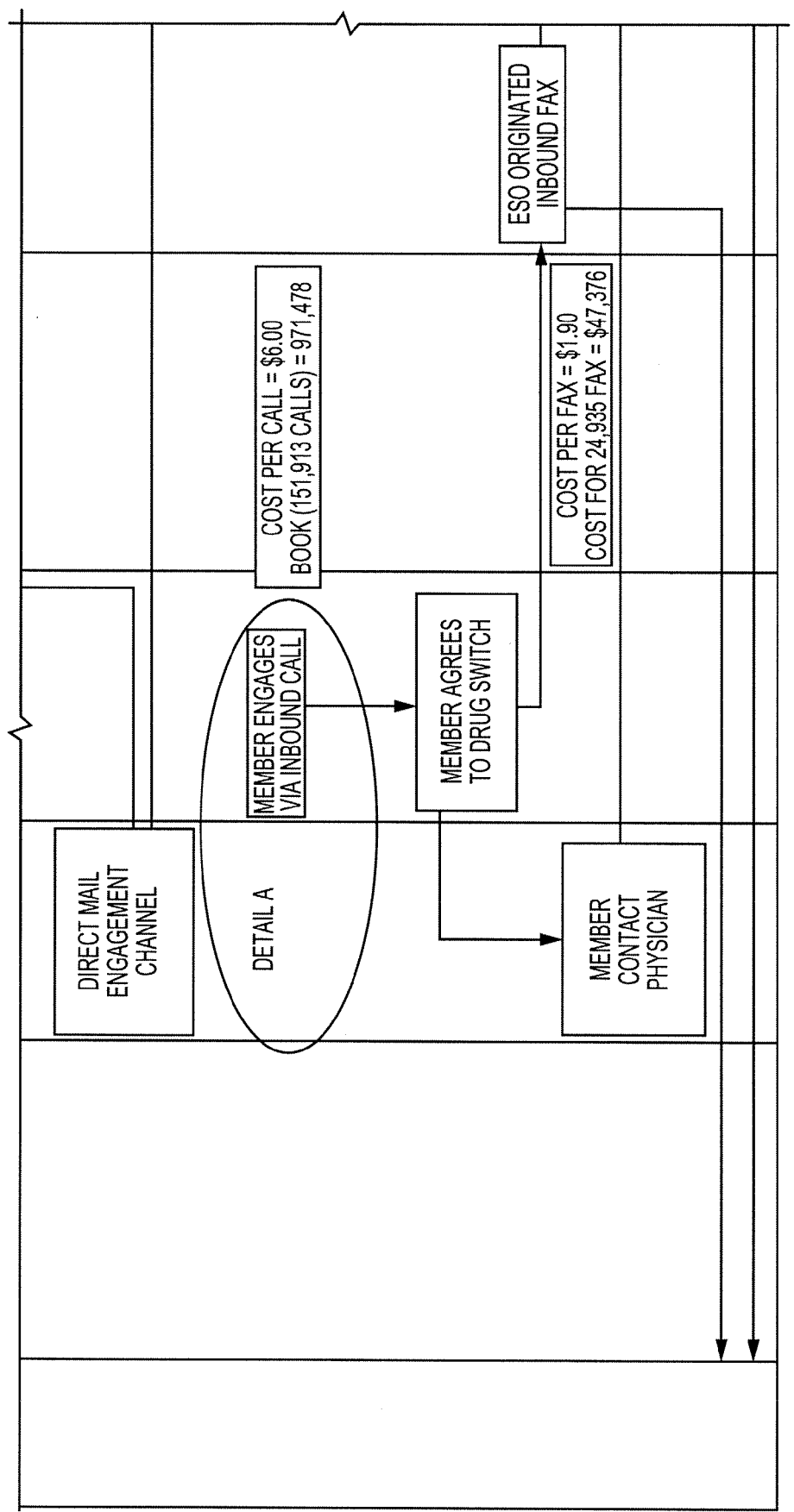

FIG. 27 gives further details of the savings achieved by members who did not use the My Rx Choices. Members were given calls by benefit specialists, of those who accepted calls, about half accepted a savings opportunity. FIG. 28 gives further details of the savings achieved by members who used the My Rx Choices.

Other embodiments, extensions and modifications of the ideas presented above are comprehended and within the reach of one versed in the art upon reviewing the present disclosure. Accordingly, the scope of the present invention in its various aspects should not be limited by the examples and embodiments presented above. The individual aspects of the present invention and the entirety of the invention should be regarded so as to allow for such design modifications and future developments within the scope of the present disclosure. The present invention is limited only by the claims that follow.

What is claimed is:

1. A method implemented by a pharmaceutical benefits management computer system used by a pharmaceutical benefits manager, for reducing medication purchasing costs for a member of a pharmaceutical benefits plan managed by the pharmaceutical benefits manager, comprising the steps of:
   (a) analyzing using the pharmaceutical benefits management computer system, a medication prescribed to the member;
   (b) recommending at least one substitute medication for the analyzed medication, wherein the recommendation is based on the pharmaceutical benefits plan of the member, and wherein the member's pharmaceutical benefits plan of the member is managed by the pharmaceutical benefits management computer system;
   (c) receiving, from the member, at least one of an authorization and selection of a substitute medication from the at least one recommended medication;
   (d) requesting approval from at least one of an authorizing physician, a pharmacist and an authorizing health care professional for the selected substitute medication;
   (e) grouping the requested approval with a plurality of other requests received for approvals of substitute medication for a plurality of members associated with same said at least one of the authorizing physician, the pharmacist and the authorizing health care professional, wherein the other requests for approval are received from a plurality of members of pharmaceutical benefit plans managed by the pharmaceutical benefits management system, and wherein said grouping enables said same at least one of the authorizing physician, the pharmacist and the authorizing health care professional for the plurality of members, to respond to the requested approval and the other requests for at least one of the selected substitute medication and other medications;

(f) processing by the pharmaceutical benefits management computer system the response to the requested approval and the other requests for the at least one of the selected substitute medication and the other medications for the plurality of members; and (g) informing the plurality of members corresponding to the requested group approval, whether the substitute medication was approved.

2. The method of claim 1, further comprising the step of: collecting medication claim history of the member; and allowing the member to select the medication to be analyzed from the set of medications in their medication claim history.

3. The method of claim 1, further comprising the step of: facilitating the purchase and acquisition of the approved substitute medication.

4. The method of claim 3, wherein facilitating the purchase and acquisition of the approved substitute medication comprises displaying a plurality of pharmacies selling the approved substitute medication.

5. The method of claim 1, further comprising the step of: administering a questionnaire to the member before recommending the at least one substitute medication.

6. The method of claim 5, wherein the questionnaire has at least one question on medication allergies.

7. The method of claim 1, wherein recommending a least one substitute drug comprises analyzing the formulary of the member's pharmaceutical benefits plan to find a lower cost medication that is a therapeutic equivalent.

8. The method of claim 1, wherein the possible responses from the at least one of an authorizing physician, a pharmacist, and an authorizing health care professional, to the request for approval include, approve, deny, or see member.

9. The method of claim 1, wherein the recommended substitute medication is at least one of a generic drug, brand name drug, therapeutic alternative drug, and over the counter drug.

10. The method of claim 1, wherein steps (b), (c), and (g) are done over the phone.

11. The method of claim 1, wherein steps (b), (c) and (g) are done through the mail.

12. The method of claim 1, further comprising maintaining a database of responses from the at least one of an authorizing physician, a pharmacist and an authorizing health care professional; and using the database when recommending at least one lower cost substitute medication.

13. The method of claim 1, wherein grouping the requested approval with a plurality of other medication substitution requests is done by grouping substitution requests for the analyzed medication together.

14. The method of claim 1, wherein analyzing a medication prescribed to a member uses information about the member's physical condition obtained from the member's laboratory results.

15. The method of claim 1, wherein receiving, from the member, at least one of an authorization and selection of a substitute medication based on dose and strength.

16. The method of claim 1, wherein analyzing a medication prescribed to the member and recommending at least one substitute medication for the analyzed medication, is initiated by the pharmaceutical benefits manager.

17. The method of claim 16, wherein analyzing a medication prescribed to the member, and recommending at least one substitute medication for the analyzed medication, is initiated by the pharmaceutical benefits manager in response to a medication claim history of the member including a medication for a chronic condition.

18. A computer implemented system provided by a pharmaceutical benefits manager, for reducing medication purchasing costs for a member of a pharmaceutical benefits plan managed by the pharmaceutical benefits manager, comprising:

a medication analysis engine, provided by a pharmaceutical benefits manager, executing on a computer, analyzing a medication prescribed to the member;

a plurality of databases connected to the medication analysis engine, including at least a medication information database, and a client profile database comprising pharmaceutical benefits plan information for members;

recommending at least one substitute medication for the analyzed medication, wherein the recommendation is based on the client profile database and a member's pharmaceutical benefits plan, and wherein the recommendation is based on known medication substitutions, and wherein the member's pharmaceutical benefits plan is managed by the pharmaceutical benefits manager;

where the medication analysis engine receives from a client interface, operated by the member, an authorization and selection an of a substitute medication from the at least one recommended medication;

the medication analysis engine requesting approval from at least one of an authorizing physician, a pharmacist, and an authorizing health care professional, for the selected substitute medication;

an approval request with the requested approval, and a plurality of other medication substitution requests grouped together on the approval request wherein the plurality of other medication substitution requests are from a plurality of members of pharmaceutical benefit plans managed by the pharmaceutical benefits manager for a plurality of members associated with said at least one of the authorizing physician, the pharmacist and the authorizing health care professional, and wherein said grouping enables said same at least one of the authorizing physician, the pharmacist and the authorizing health care professional for the plurality of members, to respond to the requested approval and the other requests for at least one of the selected substitute medication and other medications;

the medication analysis engine processing the response to the requested approval and the other requests for the at least one selected substitute of the medication and the other medications for the members; and an interface for informing the member that the substitute medication was approved.

19. The system of claim 18, further comprising a database of medication claim history of the member, wherein the database is used to populate an interface allowing the member to select the medication to be analyzed.

20. The system of claim 18, further comprising a questionnaire from the member providing data to the medication analysis engine.

21. The system of claim 18, further comprising a database of responses, wherein the database is used when recommending at least one substitute medication.

22. The system of claim 18, further comprising a database of international classification of disease codes, the international classification of disease codes being used to recommend at least one substitute medication.

23. The system of claim 18, further comprising a database for storing both recommended and non-recommended substitute medications for a plurality of members whose medications have been analyzed.

24. The system of claim 18, further comprising a reporting engine for providing to the interface one or more substitute medications formatted appropriately for the interface.

25. The system of claim 18, further comprising a patient stratification component connected to the medication analysis engine, wherein the patient stratification component provides information used in recommending at least one substitute medication.

26. The system of claim 18, further comprising:
- a database of medication claim history of the member, wherein the database is used to populate an interface allowing the member to select the medication to be analyzed;
- a database of responses, wherein the database is used when recommending at least one substitute medication;
- a database of international classification of disease codes, the international classification of disease codes being used by the medication analysis engine to recommend at least one substitute medication;
- a database for storing both recommended and non-recommended substitute medications for a plurality of members whose medications have been analyzed; and
- a reporting engine for providing to the interface one or more substitute medications formatted appropriately for the interface.

27. The system of claim 18, further comprising a database of the member's laboratory results, wherein the results are used by the medication analysis engine to recommend a substitute drug.

28. The system of claim 18, wherein analyzing a medication prescribed to the member and recommending at least one substitute medication for the analyzed medication, is initiated by the medication analysis engine.

29. The system of claim 28, wherein the medication analysis engine analyzing a medication prescribed to the member and recommending at least one substitute medication for the analyzed medication, is initiated by the medication analysis engine in response to a medication claim history of the member including a medication for a chronic condition.

30. A method, implemented by a pharmaceutical benefits management computer system used by a pharmaceutical benefits manager, for reducing medication purchasing costs for a member of a pharmaceutical benefits plan managed by the pharmaceutical benefits manager, comprising:
(a) requesting a medication to be analyzed from a member;
(b) analyzing using the pharmaceutical benefits management computer system, the medication requested by the member;
(c) recommending at least one substitute medication for the analyzed medication, wherein the recommendation is based on the pharmaceutical benefits plan of the member, and wherein the member's pharmaceutical benefits plan of the member is managed by the pharmaceutical benefits management computer system, and on a database of known medication substitutes;
(d) receiving, from the member, at least one of an authorization and selection of a substitute medication for the at least one recommended medication;
(e) requesting approval from at least one of an authorizing physician, a pharmacist and an authorizing health care professional, for the selected substitute medication;
(f) grouping the requested approval with a plurality of other requests received for approvals of substitute medication for a plurality of members associated with same said at least one of the authorizing physician, the pharmacist and the authorizing health care professional, wherein the other requests for approval are received from a plurality of members of pharmaceutical benefit plans managed by the pharmaceutical benefits management system, and wherein said grouping enables said same at least one of the authorizing physician, the pharmacist and the authorizing health care professional for the plurality of members, to respond to the requested approval and the other requests for at least one of the selected substitute medication and other medications;
(g) processing by the pharmaceutical benefits management computer system the response to the requested approval and the other requests for the at least one of the selected substitute medication and the other medications for the plurality of members; and
(h) informing the plurality of members corresponding to the requested group approval, whether the substitute medication was approved.

31. The method of claim 30, further comprising the step of:
facilitating at least one of the acquisition and purchase of the approved substitute medication.

32. The method of claim 30, wherein the possible responses to the request for approval include approve, deny, or see member.

33. The method of claim 30, further comprising the step of:
maintaining a database of responses from the at least one of an authorizing physician, a pharmacist and an authorizing health care professional; and using the database when recommending at least one substitute medication.

34. A method, implemented by a pharmaceutical benefits management computer system used by a pharmaceutical benefits manager, for reducing medication purchasing costs for a member of a pharmaceutical benefits plan managed by the pharmaceutical benefits manager, using a wireless mobile computing device comprising:
(a) requesting a medication to be analyzed from a member using a wireless mobile computing device;
(b) analyzing using the pharmaceutical benefits management computer system, the medication requested by the member;
(c) recommending at least one substitute medication for the analyzed medication, wherein the recommendation is based on the pharmaceutical benefits plan of the member, and wherein the member's pharmaceutical benefits plan of the member is managed by the pharmaceutical benefits management computer system;
(d) receiving, from the member, at least one of an authorization and selection of a substitute medication for the at least one recommended medication;
(e) requesting approval from at least one of an authorizing physician, a pharmacist and an authorizing health care professional, for the selected substitute medication;
(f) grouping the requested approval with a plurality of other requests received for approvals of substitute medication for a plurality of members associated with same said at least one of the authorizing physician, the pharmacist and the authorizing health care professional, wherein the other requests for approval are received from a plurality of members of pharmaceutical benefit plans managed by the pharmaceutical benefits management system, and wherein said grouping enables said same at least one of the authorizing physician, the pharmacist and the authorizing health care professional for the plurality of members, to respond to the requested approval and the other requests for at least one of the selected substitute medication and other medications;

(g) processing by the pharmaceutical benefits management computer system the response to the requested approval and the other requests for the at least one of the selected substitute medication and the other medications for the plurality of members; and (h) informing the plurality of members corresponding to the requested group approval, through the interface of the wireless mobile computing device, whether the substitute medication was approved.

35. A computer implemented system for reducing medication purchasing costs for a member of a pharmaceutical benefits plan comprising:

a medication analysis engine executing on a computer, analyzing a medication prescribed to the member, the member selecting the medication from a database of medication claim history of the member, wherein the database is used to populate an interface allowing the member to select the medication to be analyzed;

a plurality of databases connected to the medication analysis engine, including at least a client profile database comprising pharmaceutical benefits plan information for members;

recommending at least one substitute medication for the analyzed medication, wherein the recommendation is based on the client profile database and a member's pharmaceutical benefits plan, and wherein the recommendation is based on known medication substitutions, and wherein at least one of the recommendations is stored in a database linked to the analyzed medication;

wherein the medication analysis engine receives from a client interface, operated by the member, an authorization and selection of a substitute medication for the at least one recommended medication;

the medication analysis engine requesting approval from at least one of an authorizing physician, a pharmacist, and an authorizing health care professional, for the selected substitute medication;

an approval request with the requested approval, and a plurality of other medication substitution requests grouped together on the approval request, for a plurality of members associated with same said at least one of the authorizing physician, the pharmacist and the authorizing health care professional, and wherein said grouping enables said same at least one of the authorizing physician, the pharmacist and the authorizing health care professional for the plurality of members, to respond to the requested approval and the other requests for at least one of the selected substitute medication and other medications;

the medication analysis engine processing the response to the requested approval and the other requests, the response being stored along with a plurality of other responses in a database of responses for the at least one selected substitute of the medication and the other medications for the members;

and an interface for informing the member that the substitute medication was approved for at least one of their purchase and acquisition.

* * * * *